US010166185B2

(12) United States Patent
Carpanzano et al.

(10) Patent No.: US 10,166,185 B2
(45) Date of Patent: Jan. 1, 2019

(54) EXCIPIENT AND ORAL SOLID DOSAGE FORMS FOR OILY DRUGS

(71) Applicant: J. Rettenmaier & Söhne GmbH + Co KG, Rosenberg (DE)

(72) Inventors: Anthony Carpanzano, Patterson, NY (US); Michael Nagel, Patterson, NY (US)

(73) Assignee: J. Rettenmaier & Söhne GmbH + Co KG, Rosenberg (DE)

( * ) Notice: Subject to any disclaimer, the term of this patent is extended or adjusted under 35 U.S.C. 154(b) by 0 days.

(21) Appl. No.: 15/178,288

(22) Filed: Jun. 9, 2016

(65) Prior Publication Data

US 2016/0361261 A1 Dec. 15, 2016

Related U.S. Application Data

(63) Continuation-in-part of application No. 62/173,145, filed on Jun. 9, 2015.

(51) Int. Cl.
*A61K 9/00* (2006.01)
*A61K 9/16* (2006.01)
*A61K 9/20* (2006.01)

(52) U.S. Cl.
CPC .......... *A61K 9/1652* (2013.01); *A61K 9/0053* (2013.01); *A61K 9/1611* (2013.01); *A61K 9/2009* (2013.01); *A61K 9/2054* (2013.01)

(58) Field of Classification Search
None
See application file for complete search history.

(56) References Cited

U.S. PATENT DOCUMENTS

| 4,994,276 | A | 2/1991 | Baichwal et al. |
| 5,128,143 | A | 7/1992 | Baichwal et al. |
| 5,478,574 | A | 12/1995 | Baichwal et al. |
| 5,585,115 | A | 12/1996 | Sherwood et al. |
| 5,725,883 | A | 3/1998 | Staniforth et al. |
| 5,725,884 | A | 3/1998 | Sherwood et al. |
| 5,741,524 | A | 8/1998 | Staniforth et al. |
| 5,858,412 | A | 1/1999 | Staniforth et al. |
| 5,866,166 | A | 2/1999 | Staniforth et al. |
| 5,948,438 | A | 9/1999 | Staniforth et al. |
| 6,103,219 | A | 8/2000 | Sherwood et al. |
| 6,106,865 | A | 8/2000 | Staniforth et al. |
| 6,217,909 | B1 | 4/2001 | Sherwood et al. |
| 6,358,533 | B2 | 3/2002 | Sherwood et al. |
| 6,395,303 | B1 | 5/2002 | Staniforth et al. |
| 6,471,994 | B1 | 10/2002 | Staniforth et al. |
| 6,521,261 | B2 | 2/2003 | Sherwood et al. |
| 6,746,693 | B2 | 6/2004 | Staniforth et al. |
| 6,858,231 | B2 | 2/2005 | Sherwood et al. |
| 6,866,867 | B2 | 3/2005 | Staniforth et al. |

(Continued)

OTHER PUBLICATIONS

Rowe et al. "Colloidal Silicon Dioxide", The Handbook of Pharmaceutical Excipients, The Pharmaceutical Press: 6th Ed, 2009, pp. 185-188.*

*Primary Examiner* — Carlos A Azpuru
*Assistant Examiner* — Casey S Hagopian
(74) *Attorney, Agent, or Firm* — Davidson, Davidson & Kappel, LLC

(57) ABSTRACT

The present invention is directed to an excipient which can be used to manufacture tablets containing oily active ingredients such as oily drugs, and pharmaceutical compositions containing the same.

16 Claims, 5 Drawing Sheets

(56) References Cited

U.S. PATENT DOCUMENTS

| | | |
|---|---|---|
| 6,936,277 B2 | 8/2005 | Staniforth et al. |
| 2001/0001664 A1 | 5/2001 | Sherwood et al. |
| 2003/0091624 A1* | 5/2003 | Szymczak .............. A61K 9/143 424/465 |
| 2007/0190080 A1 | 8/2007 | Friedman |
| 2009/0324729 A1* | 12/2009 | Koziara ............... A61K 9/1611 424/490 |
| 2010/0196475 A1 | 8/2010 | Grenier et al. |

* cited by examiner

EXCIPIENT AND ORAL SOLID DOSAGE FORMS FOR OILY DRUGS

FIELD OF THE INVENTION

This application claims the benefit of U.S. Provisional Application No. 62/173,145, filed Jun. 9, 2016, incorporated by reference in its entirety. The present invention is related to a novel excipient for use in the manufacture of pharmaceuticals and nutraceuticals, and in particular, solid dosage forms such as tablets which include one or more active ingredients which are water-insoluble or oil-dissolved, or are themselves oils.

BACKGROUND OF THE INVENTION

The present invention relates to a novel excipient for use in the manufacture of pharmaceuticals and/or nutraceuticals, and in particular, solid dosage forms such as tablets which include one or more active ingredients.

In order to prepare a solid dosage form containing one or more active ingredients (such as drugs), it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to insure that the solid dosage form remains intact after compression.

In the case of tablets, the tablet is formed by pressure being applied to the material to be tabletted on a tablet press. A tablet press includes a lower punch which fits into a die from the bottom and an upper punch having a corresponding shape and dimension which enters the die cavity from the top after the tableting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most drugs have none or only some of these properties, methods of tablet formulation have been developed in order to impart these desirable characteristics to the material(s) which is to be compressed into a solid dosage form. Typically, the material to be compressed into a solid dosage form includes one or more excipients which impart the free-flowing, lubrication, and cohesive properties to the drug(s) which is being formulated into a dosage form.

Lubricants are typically added to avoid the material(s) being tabletted from sticking to the punches. Commonly used lubricants include magnesium stearate and calcium stearate. Such lubricants are commonly included in the final tabletted product in amounts of less than 1% by weight.

In addition to lubricants, solid dosage forms often contain diluents. Diluents are frequently added in order to increase the bulk weight of the material to be tabletted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethylcellulose.

There are three general methods of preparation of the materials to be included in the solid dosage form prior to compression: (1) dry granulation; (2) direct compression; and (3) wet granulation.

Dry granulation procedures may be utilized where one of the constituents, either the drug or the diluent, has insufficient cohesive or flow properties to be tabletted. The method includes mixing the ingredients, slugging the ingredients, dry screening, lubricating and finally compressing the ingredients.

In direct compression, the powdered material(s) to be included in the solid dosage form is compressed directly without modifying the physical nature of the material itself.

The wet granulation procedure includes mixing the powders to be incorporated into the dosage form in, e.g., a twin shell blender or double-cone blender and thereafter adding solutions of a binding agent to the mixed powders to obtain a granulation. Thereafter, the damp mass is screened, e.g., in a 6- or 8-mesh screen and then dried, e.g., via tray drying, the use of a fluid-bed dryer, radio-frequency dryer, microwave, vacuum, or infra-red dryer.

The use of direct compression is limited to those situations where the drug or active ingredient has a requisite crystalline structure and physical characteristics required for formation of a pharmaceutically acceptable tablet. On the other hand, it is well known in the art to include one or more excipients which make the direct compression method applicable to drugs or active ingredients which do not possess the requisite physical properties. For solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed.

Typically, however, excipients are added to the formulation in order to impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

A limitation of direct compression as a method of tablet manufacture is the size of the tablet. If the amount of active ingredient is high, a pharmaceutical formulator may choose to wet granulate the active with other excipients to attain an acceptably sized tablet with the desired compact strength. Usually the amount of filler/binder or excipients needed in wet granulation is less than that required for direct compression since the process of wet granulation contributes to some extent toward the desired physical properties of a tablet. Thus, despite the advantages of direct compression (such as reduced processing times and costs), wet granulation is widely used in the industry in the preparation of solid dosage forms. Many of those skilled in the art prefer wet granulation as compared to direct compression because this method has a greater probability of overcoming any problems associated with the physical characteristics of the various ingredients in the formulation, thereby providing a material which has the requisite flow and cohesive characteristics necessary to obtain an acceptable solid dosage form.

The popularity of the wet granulation process as compared to the direct compression process is based on at least three advantages. First, wet granulation provides the material to be compressed with better wetting properties, particularly in the case of hydrophobic drug substances. The addition of a hydrophilic excipient makes the surface of a hydrophobic drug more hydrophilic, easing disintegration and dissolution. Second, the content uniformity of the solid dosage forms is generally improved. Via the wet granulation method, all of the granules thereby obtained should contain approximately the same amount of drug. Thus, segregation of the different ingredients of the material to be compressed (due to different physical characteristics such as density) is avoided. Segregation is a potential problem with the direct compression method. Finally, the particle size and shape of the particles comprising the granulate to be compressed are optimized via the wet granulation process. This is due to the fact that when a dry solid is wet granulated, the binder "glues" particles together, so that they form granules which when dried exhibit enhanced flow and compression characteristics.

Due to the popularity of microcrystalline cellulose, pharmaceutical formulators have deemed it desirable to include this excipient in a formulation which is wet granulated prior to tabletting.

A processed cellulose, microcrystalline cellulose, has been utilized extensively in the pharmaceutical industry as a direct compression vehicle for solid dosage forms. Microcrystalline cellulose is commercially available under the tradename Emcocel® from JRS Pharma and as Avicel® from FMC Corp. Compared to other directly compressible excipients, microcrystalline cellulose is generally considered to exhibit superior compressibility and disintegration properties.

Silicified microcrystalline cellulose is commercially available as Prosolv® SMCC and is a high functionality excipient that imparts superior flow, compaction and dispersion to a formulation. When used in direct compression, Prosolv® SMCC can replace granulations and provide uniform tablets, while significantly reducing excipient numbers and levels. Prosolv® SMCC may enable direct compression while avoiding wet granulation, and may provide increased production capacity and improved compactability. On the other hand, Prosolv® SMCC provides excellent compressibility even when wet granulated, and so is useful in wet granulated formulations, as well.

Neusilin® is a totally synthetic magnesium aluminometasilicate (MAS) with exceptional excipient properties to improve API delivery and the quality of oral solid dosage forms, commercially available from Fuji Chemical Industry Co., Ltd. Neusilin is a multifunctional excipient that can be used in both direct compression and wet granulation of solid dosage forms. Neusilin is widely used for improvement of the quality of tablets, powder, granules and capsules. In its product description, it is stated that the most suitable grade for converting oil to powder is Neusilin® US2. When the oil load is comparatively high, an addition of 0.5 to 2% UFL2 is said to improve flowability substantially. Neusilin® UFL2 alone at 0.5% can resolve sticking issues of oily formulations. Neusilin® is said to potentially resolve problems associated with tabletting and improve efficiency of poorly water soluble drugs in a solid dispersion, as well as improve dissolution and bioavailability. Neusilin® is also said to be useful in developing a Self Emulsifying Drug Delivery System (SEDDS) or a Self Nano-Emulsifying Drug Delivery System (SNEDDS), by aiding in the conversion of the liquid SEDDS/SNEDDS into a solid one. Neusilin® is further described as being safe with no reports of adverse reactions and is an accepted ingredient by the U.S. Pharmacopoeia/National Formulary and Japanese Pharmaceutical Codex. Based on the usage as an excipient in various formulations in Japan, Neusilin® up to 1.05 g can be used for oral uptake per day. (Encyclopedia of Pharmaceutical Additives, Japan, 2005). Neusilin® (Alkaline grades) is also approved as antacid active ingredient where the maximum dosage is 4 g/day. (Japanese approved list of manufacturing and import of gastrointestinal drugs). There are no established maximum oral intake limits specified by US-FDA. Neusilin® is described in U.S. Patent Publication No. 2010/0196475, hereby incorporated by reference in its entirety.

Oily drugs, or drugs which are dissolvable in oil, are typically prepared as soft gel capsules. Although there are many commonly used excipients that will absorb oils or oily drugs, these excipients can only absorb a limited amount of oil when the goal is to manufacture tablets, and many do not retain the oil sufficiently to prevent its partial loss during the compression process.

OBJECTS AND SUMMARY OF THE INVENTION

It is an object of the present invention to provide an excipient which when mixed with an oily active ingredient (or an active ingredient dissolved in an oil), will result in a free-flowing powder that can be compressed into tablets without the expression of the oil during the compression process.

It is a further object of the present invention to provide an excipient useful in the production tablets containing oily active ingredients (e.g., drugs).

It is a further object of the present invention to provide an improved microcrystalline cellulose excipient which has improved capability to absorb oily active ingredients.

It is another object of the present invention to provide an excipient which can be used to tablet oily active ingredients, where the excipient can be premanufactured.

It is a further object of the present invention to provide a solid dosage form which includes one or more oily active ingredients and the improved microcrystalline cellulose excipient of the present invention.

It is a further object of the present invention to enable manufacture of and provide an oral solid dosage form for one or more oily active ingredients which is economical to manufacture, which maintains its integrity during storage, and which possesses excellent disintegration and dissolution properties when exposed, e.g., to gastrointestinal fluid.

In accordance with the above objects and others which will be obvious to those skilled in the art, the present invention is directed to an excipient which comprises or consists of microcrystalline cellulose and a silicate-based adsorbant carrier for an oily active ingredient. In certain embodiments, the excipient further comprises or consists of an optional compressibility enhancing agent.

In certain preferred embodiments, the silicate based absorbant carrier is a magnesium aluminometasilicate, a granular or fine powder grade of a hydrophilic silica, or a mixture thereof. In certain preferred embodiments, the granular or fine powder grade of hydrophilic silica is a granular hydrophilic fumed silica. In certain embodiments, the silicate-based carrier may alternatively or further comprise hydrophilic mixed oxides of silicon dioxide ($SiO_2$) and aluminum oxide ($Al_2O_3$). In yet other embodiments, the silicate-based carrier may alternatively or further comprise a hydrophobic grade of a granular or fine powder silica (e.g., a hydrophobic fumed silica).

In certain embodiments, the excipient comprises a magnesium aluminometasilicate as the silicate-based adsorbant carrier. In certain embodiments, the excipient further includes a colloidal silicon dioxide as a compressibility enhancing agent.

In certain embodiments, the excipient comprises a granulated hydrophilic fumed silica as the silicate-based adsorbant carrier. In certain embodiments, the excipient further includes a colloidal silicon dioxide as a compressibility enhancing agent. In certain preferred embodiments, the excipient of the present invention comprises a particulate agglomerate of coprocessed microcrystalline cellulose, from about 0.5% to about 50% silicate-based adsorbant carrier, by weight of the microcrystalline cellulose, and optionally from about 0.1% to about 20% colloidal silicon dioxide, by weight.

In certain embodiments, the excipient particles have an average particle size of from about 10 microns to about 500 microns. In certain embodiments, the excipient particles have an average particle size of from about 10 microns to about 500 microns.

In certain preferred embodiments, the microcrystalline cellulose and silicate-based adsorbant carrier (and optional compressibility enhancing agent such as colloidal silicon dioxide) are in intimate association with each other (e.g., are co-processed), in the form of agglomerated particles, e.g., as attainable via a spray-drying technique.

In certain preferred embodiments, the (optional) colloidal silicon dioxide portion of the agglomerate being derived from a colloidal silicon dioxide having a particle size from about 1 nanometer (nm) to about 100 microns, based on average primary particle size. In additional preferred embodiments of the invention, the silicon dioxide has a particle from about 5 nm to about 50 microns.

In preferred embodiments, the (optional) colloidal silicon dioxide component comprises from about 0.5% to about 15% of the excipient, and most preferably from about 1% to about 5% by weight relative to the total weight of the excipient.

In preferred embodiments of the present invention, the colloidal silicon dioxide is further characterized by a surface area from about 10 m$^2$/g, to about 500 m$^2$/g, preferably from about 50 m$^2$/g to about 500 m$^2$/g, and more preferably from about 175 m$^2$/g to about 350 m$^2$/g.

In certain preferred embodiments, the compressibility enhancing agent is a colloidal silicon dioxide as described herein. In certain preferred embodiments, the colloidal silicon dioxide has surface area from about 10 m$^2$/g to about 500 m$^2$/g, and more preferably from about 175 m$^2$/g to about 350 m$^2$/g.

In certain preferred embodiments, the silicate-based adsorbant carrier is a magnesium aluminometasilicate. In certain preferred embodiments, the magnesium aluminometasilicate is, e.g., Neusilin® US2 or UFL2.

In certain preferred embodiments, the silicate-based adsorbant carrier is a granulated hydrophilic fumed silica. In certain preferred embodiments, the granulated hydrophilic fumed silica is, e.g., Aeroperl® 300, commercially available from Evonik.

In certain embodiments, the excipient comprises (in addition to the silicate-based adsorbant carrier) Prosolv® SMCC 50 (silicified microcrystalline cellulose) commercially available from JRS Pharma. This product typically has a particle size ranging from about 45 to about 80 μm.

In certain embodiments, the compressibility augmenting agent is selected from the group consisting of silicon dioxide, a surfactant, a highly polar compound, and mixtures thereof. In certain embodiments when the compressibility augmenting agent consists of said surfactant, said surfactant is present in an amount from about 0.1% to about 0.5% by weight of said microcrystalline cellulose.

In certain embodiments, the excipient composition comprises agglomerated particles of said microcrystalline cellulose, the optional compressibility augmenting agent and the silicate-based adsorbant carrier in intimate association with each other.

In certain embodiments, the agglomerated particles of the excipient composition further comprise a member of the group consisting of non-silicon metal oxides, starches, starch derivatives, polyalkylene oxides, stearic acid, kaolin, polydimethylsiloxane, silica gel, diatomaceous earth, and mixtures thereof.

In certain embodiments, the excipient composition is a physical admixture comprising microcrystalline cellulose, the silicate-based adsorbant carrier for an oily active ingredient and the (optional) compressibility augmenting agent. In certain preferred embodiments, the microcrystalline cellulose, a compressibility augmenting agent and a silicate or silicon dioxide based adsorbant carrier are in the form of agglomerated particles comprising the same. In certain preferred embodiments, therefore, the excipient composition is pre-agglomerated prior to the incorporation of an oily active ingredient(s). The agglomerated particles may have an average particle size, e.g., of from about 10 microns to about 1,000 microns, more preferably from about 10 microns to about 150 microns or may be spheronized for use in capsules.

In certain preferred embodiments wherein the excipient composition comprises a particulate agglomerate as described in the above paragraph, the excipient composition is prepared by preparing an aqueous slurry of microcrystalline cellulose in the form of a wet cake, compressibility augmenting agent(s), silicate or silicon dioxide based adsorbant carrier, and other optional ingredients, and spray-drying the ingredients to form agglomerated particles comprising the same.

The invention is further directed in part to a pharmaceutical solid dosage form, comprising an excipient composition comprising microcrystalline cellulose, a silicate-based adsorbant carrier for an oily active ingredient and an (optional) compressibility augmenting agent; and from about from about 0.5% to about 50%, or from about 1% to about 25%, and in certain embodiments from about 1% to about 35%, or from about 1% to about 22.5%, or from about 10% to about 30%, or from about 10% to about 20%, or from about 15% to about 30% of an oily active ingredient, the oily active ingredient being adsorbed onto the excipient composition. In certain preferred embodiments, the compressibility augmenting agent comprises from about 0.1% to about 20% by weight of the excipient. In certain preferred embodiments, the compressibility augmenting agent is colloidal silicon dioxide. In certain preferred embodiments, the silicate-based adsorbant carrier is a magnesium aluminometasilicate, a granulated hydrophilic fumed silica, or a mixture thereof.

In certain preferred embodiments, the microcrystalline cellulose, (optional) colloidal silicon dioxide and magnesium aluminometasilicate are in the form of agglomerated particles comprising the same, i.e., the excipient composition is a pre-agglomerated mixture of these ingredients and any further optional excipient composition ingredients as described herein. In certain preferred embodiments, the excipient particles have an average particle size of from about 10 microns to about 500 microns. In certain preferred embodiments, the colloidal silicon dioxide has surface area from about 10 m²/g to about 500 m²/g.

In certain preferred embodiments, the particles comprising the oily active agent (adsorbed onto) and the excipient composition are compressed into tablets. The tablets preferably have a hardness from about 0.7 to about 1.4 g/cm³.

In certain embodiments, the oily active ingredient is an oily material in and of itself. In other embodiments of the invention, the oily active agent comprises a low-solubility drug dissolved or dispersed in an oily solvent as described herein. The low-solubility drug has a solubility, e.g., of less than 10 mg/mL, less than 1 mg/mL, or less than 0.1 mg/mL. In yet further embodiments, the oil active ingredient is a drug which exists in a waxy state at room temperature, but becomes oily when warmed or heated.

The invention is further directed in part to a pharmaceutical solid dosage form, comprising an excipient composition comprising pre-agglomerated particles comprising microcrystalline cellulose, (optional) colloidal silicon dioxide in an amount from about 0.1% to about 20% by weight of the microcrystalline cellulose, and a magnesium aluminometasilicate in an amount from about 0.5% to about 50% by weight, an optional compressibility augmenting agent; and an oily active ingredient in an amount from about 1% to about 35%, or from about 1% to about 22.5%, or from about 15% or from about 20% to about 35%, the oily active ingredient being adsorbed onto the excipient composition. In certain preferred embodiments, the pharmaceutical composition comprises particles of the oily active ingredient adsorbed onto the excipient composition, which are compressed into tablets. The oily active ingredient may be an oily material in and of itself, or the oily active ingredient may comprise a low-solubility drug dissolved or dispersed in an oily solvent. The low-solubility drug has a solubility, e.g., of less than 10 mg/mL, less than 1 or less than 0.1 mg/mL.

The invention is further directed to a pharmaceutical solid dosage form, comprising an excipient composition comprising microcrystalline cellulose, a silicate-based adsorbant carrier selected from the group consisting of a magnesium aluminometasilicate, a granular hydrophilic silica, or a mixture thereof; and at least about 10% of an oily active ingredient, the oily active ingredient being adsorbed onto the excipient composition. In certain embodiments, the pharmaceutical solid dosage form further comprises from about 0.1% to about 20% by weight compressibility augmenting agent, which may be, e.g., colloidal silicon dioxide. The pharmaceutical solid dosage form may comprise from about 0.5% to about 50% silicate-based adsorbant carrier, by weight. When the silicate-based adsorbant carrier is a magnesium aluminometasilicate, the oily active ingredient may be present in an amount from, e.g., about 10% to about 22.5%, by weight. When the silicate-based adsorbant carrier is a granular hydrophilic fumed silica, the oily active ingredient may be present in an amount from about 10% to about 50%, by weight. The oily active agent is oily by nature or is dissolved or dispersed in an oily solvent.

Generally, when the pharmaceutical solid dosage form is a tablet, the oily active ingredient is present in an amount up to about 35% by weight. This amount of oily active ingredient may be increased when the pharmaceutical solid dosage form is not compressed and is instead incorporated in granular or powder form into a capsule.

The microcrystalline cellulose, and silicate-based adsorbant carrier which comprise the excipient composition may be a physical admixture, and in certain preferred embodiments are in the form of pre-agglomerated particles comprising the same (microcrystalline cellulose and silicate-based adsorbant carrier). The excipient particles preferably have an average particle size of from about 10 microns to about 500 microns.

The oily active agent comprises a low-solubility drug dissolved or dispersed in an oily solvent, e.g, wherein the low-solubility drug has a solubility of less than 10 mg/mL, or less than 1 mg/mL, or less than 0.1 mg/mL. When the pharmaceutical composition is compressed into tablets, the tablets preferably have a hardness from about 0.7 g/cm³ to about 1.4 g/cm³, or a hardness of from about 50 newtons to about 150 newtons, or preferably from about 80 to about 120 newtons.

The present invention is further directed to an aqueous slurry useful in the preparation of a compressible excipient useful in dry and wet granulation formulation methods, comprising a mixture of microcrystalline cellulose in the form of a wet cake (i.e. hydrocellulose or hydrolyzed cellulose), from about 0.1% to about 20% colloidal silicon dioxide by weight relative to the excipient, and from about 0.5% to about 50% silicate-based adsorbant carrier, by weight of the excipient. In certain preferred embodiments, the solids content of the aqueous slurry is from about 0.5% to about 25%, by weight, preferably from about 15% to about 20% by weight, and most preferably from about 17% to about 19% by weight.

The present invention is further directed to a mixture of an oily active ingredient(s) and an excipient comprising a mixture of coprocessed microcrystalline cellulose, from about 0.1% to about 20% compressibility augmenting agent by weight of the excipient, and from about 0.5% to about 50% silicate-based adsorbant carrier, by weight of the excipient. In certain preferred embodiments, the microcrystalline cellulose, compressibility augmenting agent and silicate-based adsorbant carrier are in intimate association with each other (e.g., are in a particulate agglomerate form) prior to the introduction of the oily active ingredient. In certain preferred embodiments, the compressibility augmenting agent is a silicon dioxide, preferably having a particle size from about 1 nm to about 100 microns. In certain preferred embodiments, the silicate-based adsorbant carrier is a magnesium aluminometasilicate (e.g., Neusilin US2 or UFL2), a hydrophilic fumed silica (e.g., Aerosil fumed silica). The oily active ingredient may comprise from about 0.1% to about 50% of the excipient, by weight.

The present invention is further directed to a granulate of an active ingredient(s) and the novel excipient described herein, wherein the active ingredient(s) and excipient have been subjected to a wet granulation procedure.

The present invention is further directed to a compressed solid dosage form comprising an active ingredient(s) and the novel excipient described herein, wherein the active ingredient(s) and excipient have been directly compressed into the solid dosage form. The compressed solid dosage form provides a suitable immediate release dissolution profile of the active ingredient(s) when exposed to aqueous solutions during in-vitro dissolution testing, and provides a release of drug in an environment of use which is considered bioavailable. In further embodiments of the invention, the dissolution profile of the solid dosage form is modified to provide a controlled or sustained release dissolution profile.

The present invention is further directed to a method of maintaining and/or enhancing the compressibility of microcrystalline cellulose in an excipient which is particularly adapted for tableting oil active agents. The method includes forming an aqueous slurry containing a mixture of microcrystalline cellulose in the form of a wet cake (i.e. hydrocellulose or hydrolyzed cellulose) and the silicate-based adsorbant carrier and (optional) colloidal silicon dioxide having a particle size from about 1 nm to about 100 microns, and drying the slurry to obtain microcrystalline cellulose-based excipient particles in which the silicon dioxide particles have been integrated with the microcrystalline cellulose particles. Within this aspect of the invention, the slurry contains from about 0.5% to about 25% by weight microcrystalline cellulose in the form of a wet cake, with amounts of from about 15% to about 20% being preferred. Furthermore, the slurry contains from about 0.25% to about 5% by weight colloidal silicon dioxide.

In certain preferred embodiments, the excipient composition provides improved bioavailability for an oily active ingredient (drug) which is adsorbed onto the excipient composition and formulated into an oral solid dosage form.

In certain preferred embodiments, the excipient composition is incorporated together with one or more oily active ingredients (e.g., drugs) into a Self Emulsifying Drug Delivery System (SEDDS) or a Self Nano-Emulsifying Drug Delivery System (SNEDDS). In certain embodiments, the oil is incorporated with an oily solvent as a Self Emulsifying Drug Delivery System (SEDDS) or a Self Nano-Emulsifying Drug Delivery System (SNEDDS). The use of such systems may improve surface area and increase bioavailability of the drug.

By "oily active ingredient" it is meant for purposes of the invention that the active ingredient that is oily in and of itself, or which is relatively insoluble in water and which dissolves in oil or is dissolved in oil, or the drug is a waxy material that is an oil when heated. Such oily active ingredients include but are not limited to drugs and nutraceuticals. The term oily active ingredient includes but is not limited to low-solubility drugs having a solubility of less than 10 mg/mL, more preferred for low-solubility drugs having a solubility of less than 1 mg/mL, and even more preferred for low-solubility drugs having a solubility of less than 0.1 mg/mL. The meaning of "low-solubility drug," is that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. When the oily active ingredient is a low-solubility active ingredient (e.g., drug), the term further encompasses the drug being dissolved or dispersed in an oily solvent.

The term "oily solvent" is meant for purposes of the present invention to encompass any pharmaceutical or food approved substance which is oily in its nature that is not mixing or dissolving with water or hydrous mediums. Such oily solvent may be natural or synthetic or semi-synthetic, in the form of liquid, semi-solid or solid at room temperature. Example of only solvents are mineral oil, vegetable oil, silicon oil, lanolin, refined animal oil, hydrocarbon esters derived from vegetable animal or marine origin. Example of vegetable oils are: isopropyl miristate, jojoba oil, almond oil, avocado oil, coconut oil, capric-caprylic tryglyceride of fractionated coconut oil, nutmeg oil, castor oil, olive oil and oleic acid, soybean oil, sunflower oil, canola oil etc. The oil may be saponifiable or unsaponifiable and liquid or solid at room temperature. Special oils are essential oils or poly unsaturated fatty acid or oils or etherified oils and modified semi-synthetic oils. Example of semi-synthetic oil is a product of inter-esterification of hydrogenated palm oil palm kernel oil ($C_8$-$C_{18}$ triglycerides) with melting point at about 30° C. to about 50° C. A further preferred class of hydrophobic solvents may be selected from the group comprising isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated ianohn alcohol, cetyl acetate, glyceryl oleate, tocopheryl linoleate, wheat germ glycerides, arachidyl propionate, myristyl lactate, isopropyl palmitate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristal myristate, isocetyl stearate and isoadipate. A further class are fatty acids include, but are not limited to, caproic acid, capric acid, caprylic acid, oleic acid, palmoic acid, stearic acid, linoleic acid, octanoic acid, decanoic acid, linolenic acid, palmitic acid, palmitoleic acid, arachidic acid, myristic acid, behenic acid and lignic acid, or fatty alcohols, and also mono and diglycerides.

By "sustained release" it is meant for purposes of the invention that the therapeutically active medicament is released from the formulation at a controlled rate such that therapeutically beneficial blood levels (but below toxic levels) of the medicament are maintained over an extended period of time, e.g., providing a 12 hour or a 24 hour dosage form.

By "bioavailable" it is meant for purposes of the invention that the therapeutically active medicament is absorbed from the formulation and becomes available in the body at the intended site of drug action.

As one of ordinary skill in the art will appreciate, the terms "microcrystalline cellulose in the form of a wet cake", "hydrocellulose", and "hydrolyzed cellulose" are synonymous, and refer to the precursor of the (dried) microcrystalline cellulose product.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
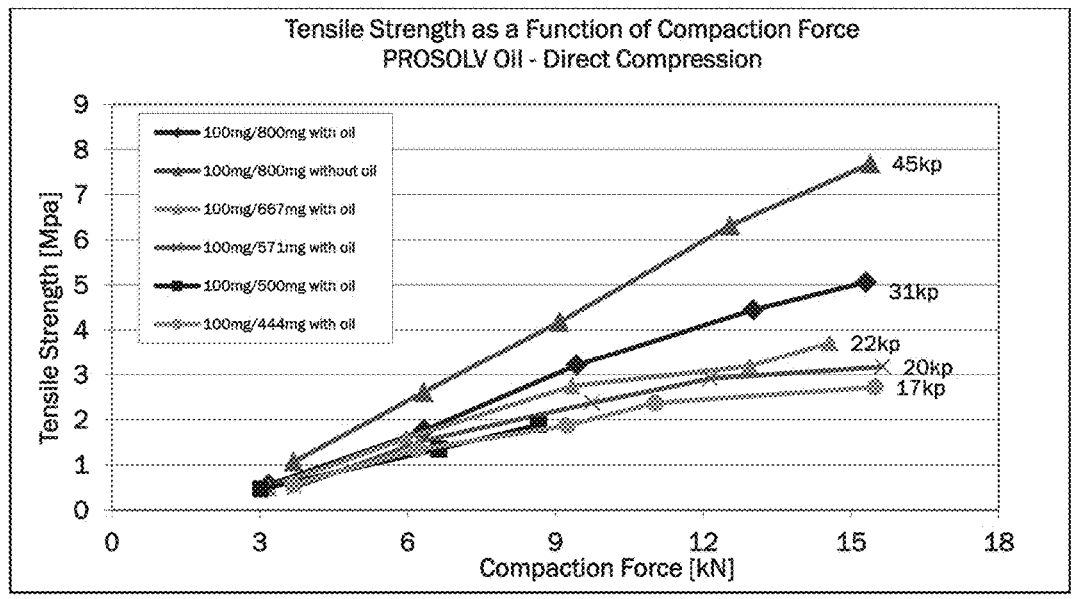
FIG. 1 graphically shows compression profiles of blended formulations of an excipient in accordance with the invention (also referred to herein as "Prosolv® Oil Excipient") of Example 1.

A major hurdle to developing tableted products containing oily active ingredients or active ingredients dissolved in an oil is the fact that there are many commonly used excipients that will adsorb oils, but when put under pressure in a tablet press, the oil gets expressed, fouling the punches and making the production of tablets impossible. Another challenge is maximizing the capacity of the powder blend to carry as much oil as possible in order to keep the size of the tablets to a minimum and make this a practical alternative to the more expensive soft-gel encapsulation process.

The present invention is directed in part to a new excipient which can be used with oily active ingredients or active ingredients which are dissolved in an oil. The excipient comprises microcrystalline cellulose, and a silicate-based adsorbant carrier (such as a magnesium aluminometasilicate and/or a hydrophilic fumed silica). The excipient optionally further comprises a compressibility augmenting agent (such as colloidal silicon dioxide).

Microcrystalline cellulose is a well-known tablet diluent and disintegrant. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and the aqueous slurry is spray dried to form dry, white odorless, tasteless crystalline powder of porous particles of a broad size distribution. In this regard, one of ordinary skill in the art will appreciate that the terms "hydrolyzed cellulose", "hydrocellulose", and "microcrystalline cellulose in the form of a wet cake" are synonymous and encompass materials prepared by partially depolymerizing cellulose obtained as pulp. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades that range in average particle size from 20 to 200 microns.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients. Typically, microcrystalline cellulose has an apparent density of about 0.28 g/cm.sup.3 and a tap density of about 0.43 g/cm$^3$. Handbook of Pharmaceutical Excipients, pages 53-55.

When utilized in pharmaceutical applications, microcrystalline cellulose is typically used as a tablet binder/diluent in wet granulation and direct compression formulations in amounts of 5-30% of the formulation, or more. However, it is known to use more or less microcrystalline cellulose in pharmaceutical products, depending upon the requirements of the formulation.

The novel agglomerated microcrystalline cellulose excipient optionally utilizes a compressibility augmenting agent which (i) physically restricts the proximity of the interface between adjacent cellulose surfaces; (ii) inhibits interactions between adjacent cellulose surfaces, for example, via the creation of a hydrophobic boundary at cellulose surfaces; or (iii) accomplishes both (i) and (ii) above.

Compressibility augmenting agents which create physical barriers between microcrystalline cellulose surfaces include silicon dioxide having a very fine particle size, e.g., from about 1 nm to about 100 microns. A most preferred silicon dioxide is colloidal silicon dioxide. Other materials of similar size may also be used instead of silicon dioxide to create the aforementioned physical barrier. In certain preferred embodiments, such other physically-acting compressibility augmenting agents will have at least some physical characteristics similar to that of silicon dioxide.

Compressibility augmenting agents which inhibit surface-to-surface interactions between surfaces of the microcrystalline cellulose include any material which has the ability, via a portion of the molecule, to bind or interact with the surface of the microcrystalline cellulose and at the same time, via another portion of the molecule, to inhibit the attraction of the cellulose surfaces, e.g., via a hydrophobic portion or "tail". Suitable compressibility augmenting agents will have an HLB value of at least 10, preferably at least about 15, and more preferably from about 15 to about 40 or greater. To date, compressibility augmenting agents which have shown the greatest effect have had relatively high HLB values, and therefore an HLB value from about 30 to about 40 or greater is most preferred. Agents which exhibit these properties include certain surfactants such as sodium lauryl sulfate and polysorbate 40, and highly polar compounds, including pharmaceutically acceptable dyes such as congo red.

In one embodiment of the invention, the compressibility augmenting agent which provides a physical barrier between adjacent cellulose surfaces is a silicon dioxide, preferably colloidal silicon dioxide. Silicon dioxide is obtained by insolubilizing dissolved silica in sodium silicate solution. When obtained by the addition of sodium silicate to a mineral acid, the product is termed silica gel. When obtained by the destabilization of a solution of sodium silicate in such a manner as to yield very fine particles, the product is termed precipitated silica. Silicon dioxide is insoluble in water. Prior to the present invention, silicon dioxide, and in particular colloidal silicon dioxide, was used mainly as a glidant and anti-adherent in tableting processes and encapsulation, promoting the flowability of the granulation. The amount of silicon dioxide included in such tablets for those applications is very limited, 0.1-0.5% by weight. Handbook of Pharmaceutical Excipients, ©1986 American Pharmaceutical Association, page 255. This is due in part to the fact that increasing the amount of silicon dioxide in the mixture to be tableted causes the mixture to flow too well, causing a phenomena known to those skilled in the tableting art as "flooding". If the mixture flows too well, a varying tablet weight with uneven content uniformity can result. All forms of silicon dioxide having an average primary particle size from about 1 nm to about 100 microns (in certain embodiments preferably from about 5 nm to about 50 nm), and/or a surface area from about 10 m$^2$/g to about 500 m$^2$/g. However, in commercial colloidal silicon dioxide products, these particles are agglomerated or aggregated to varying extents. The bulk density of the preferred class of silicon dioxides utilized in the invention ranges from about 20 g/l to about 100 g/l. The silicon dioxide utilized in the invention is preferably of the very fine particle size variety. In the more preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E. I. DuPont & Co.; and W. R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

Commercially available colloidal silicon dioxide products have, for example, a BET surface area ranging from about 50±15 m$^2$/g (Aerosil OX50) to about 400±20 m$^2$/g (Cab-O-Sil S-17) or 390±40 m$^2$/g (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0±8 g/l (Cab-O-Sil S-17) to 36.8 (e.g., Cab-O-Sil M-5). The pH of the these products at 4% aqueous dispersion ranges from pH 3.5-4.5. These commercially available products are described for exemplification purposes of acceptable properties of the preferred class of silicon dioxides only, and this description is not meant to limit the scope of the invention in any manner whatsoever.

When the novel excipient of the invention provides a compressibility which is suitable to provide pharmaceutically acceptable tablet formulations, particularly for oily drugs (as described and defined herein).

In other embodiments of the present invention, it has been discovered that the compressibility of microcrystalline cellulose which is wet granulated is significantly improved by a wider range of silicon dioxide products. Thus, in embodiments of the present invention where an improvement in overall compressibility of the microcrystalline cellulose (whether utilized in wet granulation or dry granulation) is not important, and the microcrystalline cellulose product is to be subjected to wet granulation, it has been discovered that the surface area of the silicon dioxide can be as low as about 50 m$^2$/g and the average primary particle diameter can be as large as about 100 microns. Such silicon dioxide products are also deemed to be encompassed within the scope of the invention.

In other preferred embodiments of the invention, the compressibility augmenting agent is a material which inhibits interactions between adjacent cellulose surfaces, for example, via the creation of a hydrophobic boundary or barrier at cellulose surfaces. As previously mentioned, compressibility augmenting agents which inhibit surface-to-surface interactions between surfaces of the microcrystalline cellulose include any material which has the ability, via a portion of the molecule, to bind or interact with the surface of the microcrystalline cellulose and at the same time, via another portion of the molecule, to inhibit the attraction of the cellulose surfaces, e.g., via a hydrophobic portion or "tail". Suitable compressibility augmenting agents will have an HLB value of at least 10, preferably at least about 15, and more preferably from about 15 to about 40 or greater. Compressibility augmenting agents having an HLB value from about 30 to about 40 or greater is most preferred.

Surfactants which may be used in the present invention as a compressibility augmenting agent generally include all pharmaceutically-acceptable surfactants, with the proviso that the surfactant have an HLB value of at least 10, and preferably at least about 15. In certain preferred embodiments, the HLB value of the surfactant is from about 15 to 50, and in further embodiments is most preferably from about 15.6 to about 40. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the pharmaceutical arts, sodium lauryl sulfate has been used as an emulsifying agent in amounts of up to about 0.1% by weight of the formulation. However, surfactants such as sodium lauryl sulfate have been included in coprocessed microcrystalline cellulose compositions. Moreover, surfactants have been used in the amounts described herein to improve the compressibility of microcrystalline cellulose especially in wet granulations. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone. The HLB for one acceptable non-ionic surfactant, polysorbate 40, is about 15.6.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

Those skilled in the art will further appreciate that the name and/or method of preparation of the surfactant utilized in the present invention is not determinative of the usefulness of the product. Rather, as previously mentioned, it has been surprisingly discovered that it is the physical characteristics of surfactants, especially those of the anionic class such as sodium lauryl sulfate, which are critical. In particular, it has been discovered that when an anionic surfactant such as sodium lauryl sulfate is coprocessed with microcrystalline cellulose in the amounts described herein, improved microcrystalline cellulose products of the invention result.

When the novel excipient of the invention utilizes an anionic surfactant, it has been found that the resultant excipient product surprisingly provides a compressibility which is substantially improved in preferred embodiments even in comparison to the compressibility of normal "off-the-shelf" commercially available microcrystalline cellulose used in direct compression techniques. In other embodiments of the present invention, it has been discovered that the compressibility of microcrystalline cellulose which is wet granulated is significantly improved by coprocessing the microcrystalline cellulose with an anionic surfactant such as sodium lauryl sulfate.

Since microcrystalline cellulose is substantially water insoluble, the particle size of this ingredient in the well-dispersed aqueous slurry is directly related to its particle size as it was introduced into the aqueous solution. Most surfactants, on the other hand, tend to be water soluble. Sodium lauryl sulfate, for example, is relatively soluble in water (1 g/10 ml) and, therefore, dissolves in the aqueous slurry. It should be understood, however, that the coprocessed products of the present invention are not solely limited to those which contain a dissolved surfactant. The contemplated compositions can also be prepared from slurries which contain a dispersion of the surfactant as well as the microcrystalline cellulose.

Highly polar molecules having the requisite HLB value range set forth above may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is pharmaceutically acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfonic acid]disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo) naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hyroxy-6-[7-sulfonato-4-(4-sulfonatophenylazo)-1-naphthylazo]aphthalene-1,7-disulfonate); Carmoisine (chemical name: Disodium 4-hydroxy-3-(4-sulfanato-1-naphythylazo) Naphthalene-1-sulfonate); Amaranth (chemical name: Trisodium 2-hydroxy-1-(4-sulfonato-1-naphthylazo)naphthalene-3,6-disulfonate); and mixtures thereof.

Other highly polar molecules having the requisite HLB value range set forth above which may be utilized as the compressibility augmenting agent include the active agents themselves. For example, it is well-known to those skilled in the art that certain classes of pharmaceuticals, such as anti-pyschotic drugs, are highly polar in nature and may be utilized as a compressibility augmenting agent in accordance with this invention.

One skilled in the art will appreciate that other classes of highly polar compounds may be useful in reducing the surface-to-surface interactions (including hydrogen-bonding) between cellulose surfaces. Such obvious modifications of the present invention are deemed to be within the contemplated scope of the appended claims.

Other compressibility augmenting agents encompassed herein include calcium carbonate, as described, e.g., in U.S. Pat. No. 5,747,067, hereby incorporated by reference, (particulate pharmaceutical tablet excipient compositions comprising co-processed microcrystalline cellulose and particulate USP calcium carbonate having a particle size distribution of 7 to 22 microns wherein the range of calcium carbonate to microcrystalline cellulose is 70:30 to 90:10). Also encompassed within the term compressibility augmenting agents is calcium phosphate. U.S. Pat. No. 8,632,818, hereby incorporated by reference, describes a composition useful as a pharmaceutical excipient in the preparation of tablets that are prepared by multiple compaction steps consisting of a physical blend of particles of at least one calcium phosphate and particles of microcrystalline cellulose, wherein the particles of at least one calcium phosphate have a median particle size as measured by laser diffraction of not greater than about 20 microns, and wherein tablets containing said composition have a higher tensile strength after recompaction at a tableting pressure of 120 MPa than the same tablet consisting of a physical blend of microcrystalline cellulose and a calcium phosphate having a median particle size as measured by laser diffraction of greater than about 20 microns. Yet another compressibility augmenting agent encompassed herein are sugar alcohols such as mannitol. U.S. Pat. No. 8,932,629, hereby incorporated by reference, describes a co-processed excipient composition consisting essentially of a spray dried particulate of co-processed microcrystalline cellulose and at least one sugar alcohol containing four to six carbon atoms, in which: the ratio of microcrystalline cellulose to the at least one sugar alcohol is 70:30 to 95:5. Yet another compressibility augmenting agent encompassed herein is calcium alginate, as described in U.S. Pat. No. 5,985,323, hereby incorporated by reference (excipient composition comprising particles of a dried aqueous slurry consisting essentially of unattrited microcrystalline cellulose wetcake and a low viscosity alginate selected from the group consisting of low viscosity sodium alginate and a sodium, calcium salt complex of low viscosity sodium alginate in which the low viscosity alginate has a viscosity in the range of 40 to 80 cps). This list is meant to be exemplary and is not meant to be limiting in any manner, whatsoever.

The silicate-based adsorbant carrier is a material that allows an oily active ingredient, (e.g., an active ingredient that is oily in and of itself, or which is relatively insoluble in water and which dissolves in oil or is dissolved in oil) to be adsorbed into the excipient and which allows for the composition (e.g., excipient of the invention plus one or more active agents plus any further optional pharmaceutically acceptable excipients) to be a free-flowing powder which can be tabletted or which can be filled into a capsule.

One preferred silicate-based adsorbant carrier useful in the excipients and formulations of the present invention is magnesium aluminometasilicate. This material is described in US Patent Publication No. 2010196475, hereby incorporated by reference in its entirety. Magnesium aluminometasilicate can be described by the chemical formula $Al_2O_3 \cdot MgO \cdot 2SiO_2 \cdot xH_2O$ and preferably the aluminium oxide is present in the range of from 25% to 40%, the magnesium oxide present in the range of from 10% to 15%, and the silicon dioxide is present in the range of from 25% to 40%. As a substance that absorbs moisture, these percentages are based on drying the substance at 110° C. for 7 hours. In one preferred embodiment of the invention the magnesium aluminometasilicate may be Neusilin® as produced and commercially available from Fuji Chemical Industry Co., Ltd. (www.fujichemusa.com). In one especially preferred embodiment, the silicate-based adsorbant carrier is a magnesium aluminometasilicate commercially available under the tradename Neusilin® US2 or UFL2.

In another especially preferred embodiment, the silicate-based adsorbant carrier is a granular or fine powder grade of a hydrophilic silica (silicon dioxide). Particularly preferred in certain embodiments is a granular hydrophilic fumed silica. An example of a preferred commercially available hydrophilic silica is a granular hydrophilic fumed silica such as Aeroperl® (a granulated hydrophilic fumed silica (silicon dioxide) commercially available from Evonik Industries. In certain preferred embodiments, the silicate-based adsorbant carrier is Aeroperl® 300 Pharma or 300/30, which have an average particle size of about 30 μm. Other hydrophilic fumed silicas are commercially available from Cabot Corporation under the tradename Cab-O-Sil®, such as Cab-O-Sil H-5, M-5, M-5DP, M-5F, M-5P, M-7D.

In other embodiments, the granular or fine powder grade of a hydrophilic silica is a colloidal grade hydrophilic silica, such as one or more Aerosil® products commercially available from Evonik Industries, e.g., Aerosil® 90, 130, 200, 255, 300, OX 50, TT 600, 200 F, 380 F, 200 Pharma, or 300 Pharma. Such hydrophilic fumed silica products have BET surface areas from about 75 to about 410 m$^2$/g. In certain preferred embodiments, the amount of granulated hydrophilic fumed silica contained in the excipient of the invention is from about 10% to about 50%, and in certain embodiments from about 20% to about 35%.

Other silicate-based adsorbant carriers that may be used include but are not limited to Zeofree® 80, 110SD, 200, 265, 5161, 5162, 5170, 5191 and/or 9193 (synthetic silicon dioxides commercially available from Huber), and Zeothix® 177 (a synthetic amorphous silica with sodium sulfate commercially available from Huber). Also, Zeolex® 7, 201, 23A, 23D and/or 7A (synthetic sodium aluminosilicates) may be used. Also, commercially available products from Grace such as Syloid® 244 FP and/or XDP.

In certain embodiments, the silicate-based carrier may alternatively or further comprise hydrophilic mixed oxides of silicon dioxide ($SiO_2$) and aluminum oxide ($Al_2O_3$). Examples of commercially available hydrophilic fumed mixed oxides include those commercially available from Evonik as Aerosil® MOX 80, MOX 170 and/or COK 84.

In yet other embodiments, the silicate-based carrier may alternatively or further comprise a hydrophobic grade of a granular or fine powder silica (e.g., a hydrophobic fumed silica). Examples of hydrophobic silica include hydrophobic fumed silica, such as those commercially available as Aerosil® R 972, R974,m R 104, R 106, R202, R 208, R 805, R 812, R 812 S, R 816, R 7200, R 8200, R 9200, R 711, SY 50, NY 50, NY 50 L, RY 200, RY 200 S, RX 50, NAX 50, RX 200, NA 50 H, RA 200 H, NA 130 K, NA 200 Y, NX 130, RY 200 L, R 709, and/or R 976 S.

In certain embodiments, the excipient is a physical mixture of microcrystalline cellulose, compressibility augmenting agent and a silicate-based adsorbant carrier. In other embodiments, the microcrystalline cellulose, compressibility augmenting agent and silicate-based adsorbant is a co-processed blend. The co-processed blends generally show a slightly higher oil carrying capacity that the physical mixtures, and produce very satisfactory tablets.

The process for preparing the co-processed composition involves forming a well-dispersed aqueous slurry of microcrystalline cellulose, the optional compressibility augmenting agent, and the silicate-based adsorbant carrier. The slurry may be formed by using microcrystalline cellulose wetcake formed in the hydrolysis step during the manufacture of microcrystalline cellulose, or in may be formed by re-slurrying dried microcrystalline cellulose. The relative amounts of the two components are adjusted in the slurry to yield the specific weight ratio desired in the final dried co-processed composition. In some instances, it may be desirable to form the slurry under conditions of low shear. The aqueous slurry may be prepared by first preparing the slurry of microcrystalline cellulose and thereafter adding the compressibility augmenting agent and/or the silicate-based adsorbant carrier, or by mixing these ingredients together in a (e.g., pharmaceutically acceptable) aqueous medium to form the aqueous slurry.

Both microcrystalline cellulose in the form of a wet cake (i.e hydrolyzed cellulose or hydrocellulose) and silicon dioxide are substantially water insoluble. Therefore, the particle size of these ingredients as present in the well-dispersed aqueous slurry is directly related to the particle size of these two ingredients as they were introduced into the aqueous solution. There is no appreciable dissolution of either ingredient in the aqueous slurry.

After a uniform mixture of the ingredients is obtained in the slurry (suspension), the suspension is dried to provide a plurality of microcrystalline cellulose-based excipient particles having enhanced compressibility. Preferably, the slurry is dried using spray-drying techniques, which are well known to those skilled in the art. Other drying techniques, however, such as flash drying, ring drying, tray drying, vacuum drying, radio frequency drying, and microwave drying, may be alternatively used.

The microcrystalline cellulose is preferably wetcake from a conventional microcrystalline cellulose manufacturing process. Wetcake is microcrystalline cellulose that has not yet been dried to yield conventional microcrystalline cellulose as a free-flowing powder. The particle size of the microcrystalline cellulose used in the aqueous slurry is ordinarily that which is encountered in conventional microcrystalline cellulose manufacture. pH adjustment of the wetcake can be made before, during, or after the sugar alcohol addition, preferably before, as representative of conventional MCC manufacturing processes.

The total solids content of the aqueous slurry is preferably at least 10 wt %, based on the total slurry weight, and is more preferably at least 20 wt % solids. The higher solids content levels are desirable since the amount of water that must be removed during the drying step is accordingly reduced. The upper limit on solids content in the aqueous slurry is typically determined by the operating constraints of the drying apparatus used. With the preferred spray drying procedure, solids contents of about 20 to about 30 weight % are representative for aqueous slurries that can be readily processed. Ambient or elevated slurry temperatures, of from about 10° C. to about 80° C. may be used, and higher slurry temperatures may be desirable with certain types of drying equipment.

The drying of the well-dispersed aqueous slurry is preferably accomplished by spray drying. Conventional spray drying equipment may be used. Operating procedures familiar to those skilled in the spray drying art are applicable to the spray drying step of this process. Drier outlet temperature is ordinarily used to control the residual moisture level obtained in the co-processed composition.

In the spray-drying process, the aqueous dispersion of microcrystalline cellulose in the form of a wet cake, (optional) compressibility augmenting agent (e.g., colloidal silicon dioxide) and silicate-based adsorbent carrier (e.g., magnesium alumino metasilicate) are brought together with a sufficient volume of hot air to produce evaporation and drying of the liquid droplets. The highly dispersed slurry of microcrystalline cellulose in the form of a wet cake, (optional) compressibility augmenting agent (e.g., colloidal silicon dioxide) and silicate-based adsorbent carrier (e.g., magnesium alumino metasilicate) are pumpable and capable of being atomized. It is sprayed into a current of warm filtered air, which supplies the heat for evaporation and conveys a dried product to a collecting device. The air is then exhausted with the removed moisture. The resultant spray-dried powder particles are approximately spherical in shape and are relatively uniform in size, thereby possessing excellent flowability. The coprocessed product comprises or consists of microcrystalline cellulose, compressibility augmenting agent (e.g., colloidal silicon dioxide) and silicate-based adsorbent carrier (e.g., magnesium alumino metasilicate) in intimate association with each other.

Depending upon the amount and type of drying, the concentration of the microcrystalline cellulose, (optional) compressibility augmenting agent (e.g., colloidal silicon dioxide) and silicate-based adsorbant carrier in the slurry may have different particle sizes, densities, pH and moisture content. Spray drying is an especially preferred method for removing water from the aqueous slurry and thereby accomplishing the drying step.

Spray drying the well-dispersed aqueous slurry produces a co-processed composition having a loose bulk density of less than or equal to 0.60 g/cm$^3$, suitably 0.20 g/cm$^3$ to 0.60 g/cm$^3$. This produces a composition having a preferred compactability in the presence of lubricant compared to either a dry blend of the materials or the corresponding wet granulate. The loose bulk density may be less than 0.55 g/cm$^3$, less than 0.50 g/cm$^3$, less than 0.45 g/cm$^3$, less than 0.40 g/cm$^3$, less than 0.35 g/cm$^3$, less than 0.30 g/cm$^3$, and less than 0.25 g/cm$^3$.

The co-processed composition recovered from the drying operation is a free-flowing particulate solid. Particle size of the product is a function of the spray drier settings, which can be controlled by those skilled in the art such as adjusting feed rates and atomizer disc speeds during spray drying.

It is most preferred in the present invention that the microcrystalline cellulose, (optional) compressibility enhancing agent and the silicate-based adsorbent carrier are coprocessed, resulting in an intimate association of these ingredients, rather than being combined, e.g., as a dry mixture. In preferred embodiments of the present invention, the aqueous slurry of the microcrystalline cellulose in the form of a wet cake, (optional) compressibility enhancing agent (e.g., colloidal silicon dioxide) and silicate-based adsorbent carrier (e.g., magnesium aluminometasilicate) are introduced into the spray dryer as a single aqueous medium. However, it is possible to separately introduce each ingredient into separate aqueous medium which are then combined. Other procedures for combining the microcrystalline cellulose in the form of a wet cake (i.e. hydrocellulose or hydrolyzed cellulose) and silicon dioxide known to those skilled in the art are deemed to be equivalent to the spray-drying technique described above, and are further deemed to be encompassed by the appended claims.

In certain preferred embodiments of the present invention, the coprocessing of the microcrystalline cellulose and silicon dioxide is accomplished by forming a well-dispersed aqueous slurry of microcrystalline cellulose in the form of a wet cake compressibility augmenting agent (e.g., colloidal silicon dioxide) and silicate-based adsorbent carrier (e.g., magnesium alumino metasilicate and/or hydrophilic fumed silica), and thereafter drying the slurry and forming a plurality of microcrystalline cellulose-based excipient particles. Typically, microcrystalline cellulose in the form of a wet cake is first added to an aqueous solution so that a slurry or suspension containing from about 0.5% to about 25% microcrystalline cellulose in the form of solids is obtained. Preferably, the slurry or suspension contains from about 15% to 20% microcrystalline cellulose in the form of a wet cake and most preferably from about 17% to about 19% microcrystalline cellulose in the form of a wet cake. At this stage, it is often desirable to adjust the pH of the slurry to about neutral with ammonium hydroxide, sodium hydroxide, and mixtures thereof or the like. The suspension is kept under constant agitation for a sufficient time to assure a uniform distribution of the solids prior to being combined with the (optional) compressibility augmenting agent (e.g., colloidal silicon dioxide) and silicate-based adsorbent carrier (e.g., magnesium alumino metasilicate).

At this point, the (colloidal) silicon dioxide may be added to the suspension or slurry, e.g., in amounts ranging from 0.1% to about 20% by weight, based on the amount of microcrystalline cellulose. Amounts of silicon dioxide from about 0.5% to about 10% are preferred while amounts of from about 1.25% to about 5% by weight are especially preferred. The silicon dioxide is preferably in colloidal form prior to addition to the slurry. The microcrystalline cellulose in the form of a wet cake and colloidal silicon dioxide are we dispersed in the slurry or suspension prior drying and forming the novel particles.

The amount of silicate-based adsorbant carrier added to the slurry may be in an amount up to about 50% of the excipient, by weight. Preferably, the amount of silicate-based adsorbant carrier added to the slurry may be in an amount from about 5% to about 50% of the excipient, by weight, and in certain embodiments most preferably from about 12% to about 23% of the excipient, by weight. In certain embodiments, the silicate-based adsorbant carrier may be added after the incorporation of the compressibility enhancing agent (e.g., silicon dioxide) to the slurry.

The average particle size of the excipient of the present invention ranges from about 10 microns to about 1000 microns. Particle sizes of about 10-500 microns are preferred, particle sizes of about 30-250 microns are more preferred and particle sizes of about 40-200 microns are most preferred. It will be appreciated by those of ordinary skill in the art that the drying of the microcrystalline cellulose in the form of a wet cake-silicon dioxide suspension results in a random size distribution of the novel excipient particles being produced. For example if spray drying techniques are used, droplet size, temperatures, agitation, dispersion, air flow, atomizer wheel speed, etc. will effect final particle size. Furthermore, it is within the scope of the invention to sort or mechanically alter the dried particles according to ranges of particle sizes depending upon end uses. The particle size of the integrated excipient is not narrowly critical, the important parameter being that the average size of the particle must permit the formation of a directly compressible excipient which forms pharmaceutically acceptable tablets.

The excipient of the present invention preferably has a bulk (loose) density ranging from about 0.2 g/ml to about 0.6 g/ml, and most preferably from about 0.35 g/ml to about 0.55 g/ml. The novel excipient preferably has a tapped density ranging from about 0.2 g/ml to about 0.6 g/ml, and most preferably from about 0.35 g/ml to about 0.55 g/ml. The pH of the particles is most preferably about neutral, although granulates having a pH of from about 3.0 to about 8.5 are possible. The moisture content of the excipient particles will preferably broadly range from about 0.5% to about 15%, preferably from about 2.5% to about 6%, and most preferably from about 3.0% to about 5% by weight.

The novel excipient preferably comprises a particulate agglomerate of coprocessed, microcrystalline cellulose, from about 5% to about 50%, or from about 10% to about 50% and in certain embodiments from about 20% to about 35%, and in other embodiments from about 25% to about 35%, and in certain embodiments preferably from about 12% to about 23% silicate-based adsorbent carrier (e.g., magnesium aluminometasilicate or granular hydrophilic silica), by weight. The novel excipient may optionally further comprise from about 0.1% to about 20%, and preferably from about 0.25% to about 5% compressibility augmenting agent.

The novel excipient in accordance with the invention is free-flowing and directly compressible. Accordingly, the excipient may be mixed, in the desired proportion with an active agent and optional lubricant (blended or dry granulated), and then directly compressed into solid dosage forms. In preferred embodiments of the present invention, the excipient of the present invention represents an augmented microcrystalline cellulose having improved compressibility which allows for the tableting of an oily active agent as defined in herein. More particularly, the excipient of the present invention adsorbs oily active agents (e.g., oily drugs or oily compounds, or active agents/drugs/compounds dissolved in oil), resulting in a free-flowing powder that can be compressed into tablets or filled into capsules on a routine basis. Furthermore, in certain embodiments, conversion of this oil dosage form (excipient plus active agents) into tablets via this excipient may provide enhanced intrinsic solubility, and faster/better bioavailability. From a business standpoint this would be valuable to companies who could turn their problematic, slow to produce, relatively expensive soft-gel formulations into less problematic, faster and cheaper to produce tablets.

In general, commercially available pharmaceutical products which contained active ingredient(s) which are oils in soft-gel capsules have an upper limit of a dose of the oily active ingredient of about 100 mg. Most common adsorbents (kaolin, bentonite, diatomaceous earth, etc) can only "carry" to about 10% of their weight in an adsorbed compound or oil. Adsorbant carriers generally have an ability to adsorb at least their own weight in oil (it has been found that Neusilin® adsorbs about 3.2 times its weight of oily drug, whereas common adsorbants only held 10% of their own weight of other products). With this in mind, the oil-carrying capacity of the present excipient is dictated, e.g., by how much silicate-based adsorbant carrier can be loaded into the excipient and still make robust tablets under normal operating ranges.

In certain preferred embodiments, the excipient is combined with at least one oily active ingredient, optional additional (non-oily) active agent(s), and optional pharmaceutically acceptable excipients and tableted into suitably sized tablets. It has been determined that using just the dry blended excipient of the invention, the excipient alone functioned well with about a 20% load of silicate-based adsorbant carrier (e.g., Neusilin), and it was hypothesized that about 100 grams of excipient containing about 20 grams of silicate-based adsorbant carrier (e.g., Neusilin) could adsorb at least 60 grams of oil. It was determined that if the excipient of the invention were loaded to its (above-mentioned) calculated capacity based on Neusilin content, the oil would get expressed out during compression resulting in a failed tablet run. At this point, the level of oil was titrated down to a point at which no oil would be expressed from the blend during compression. With respect to the dry-blended excipient, a loading level of 100 mg oil in a 571 mg tablet (about a 17.5% load of oil) was achieved, before any oil would be expressed during compression.

In certain preferred embodiments, the excipient is prepared by spray-drying (as opposed to a dry-blending process) and it was found that the oil-loading capacity (load at which oil would get expressed from the tablets) during compression was increased significantly. This proved to be a loading of 100 mg in a 444 mg tablet (about 22.5% oil loading), but may be very close to the threshold value at which oil may come out, when the silicate-based adsorbant carrier is Neusilin. Accordingly, in certain preferred embodiments, the oil loading goal for the excipient of the invention is to provide a pharmaceutically acceptable tablet with up to about 20% oil loading (e.g., 100 mg oil in a 500 mg tablet), and even as high as about 22.5% oil loading or more.

In other preferred embodiments, the amount of oil loading of the oily active ingredient into the final product (e.g., pharmaceutically acceptable tablet) may be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 20.5%, about 21%, about 21.5%, about 22%, about 22.5%, about 23%, about 23.5%, about 24%, about 24.5%, about 25%, about 25.5%, about 26%, about 26.5%, about 27%, about 28%, about 28.5%, about 29%, about 29.5%, about 30%, about 30.5%, about 31%, about 31.5%, about 32%, about 32.5%, about 33% about 33.5%, about 34%, about 34.5%, and about 35%, for example.

In preferred embodiments, acceptable tablets are prepared which include the excipient of the present invention and an oil active ingredient(s), which can be manufactured, e.g., without fouling the press with oil. Acceptable tablets (½" diameter @ 10-13kP) have been manufactured using compression forces of as low as about 8-10 kNewtons. This is in the low end of the forces commonly used in industry to produce acceptable tablets.

In certain preferred embodiments, the excipient of the invention provides improved bioavailability for an oily drug when combined in the same in suitable proportions as described herein and prepared as a pharmaceutical dosage form for oral administration.

In preferred embodiments, the excipient is combined with an active ingredient(s) that is an oily active ingredient/agent or an active ingredient/agent that is dissolvable in an oil. Such oily active ingredients which may be incorporated together with the excipient of the present invention include but are not limited to systemically active therapeutic agents, locally active therapeutic agents, nutraceuticals, disinfecting agents, chemical impregnants, cleansing agents, deodorants, fragrances, dyes, animal repellents, insect repellents, a fertilizing agents, pesticides, herbicides, fungicides, and plant growth stimulants, and the like. In certain preferred embodiments, the active agent is one or more drug(s), a food supplement(s), a medical food(s), or a nutraceutical(s). As used herein, the term oily medicament means a medicament that is hydrophobic and that is liquid at physiological pH, temperature and osmolality.

Hundreds of medically useful compounds are discovered each year, but clinical use of these drugs is possible only if a drug delivery vehicle is developed to transport them to their therapeutic target in the human body. This problem is particularly critical for drugs which are water insoluble or poorly water soluble. Such compounds are generally referred to by those skilled in the art as "lipophilic", "hydrophobic", or in their most difficult form, "amphiphobic". In order to make oral dosage forms of such drugs, it is often found necessary to formulate the same in an oil which is then encapsulated. For example, soft gel or soft gelatin capsules may be used to encapsulate the oil-based drug. Such soft gel capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

A few examples of therapeutic substances that are considered to be water insoluble are ibuprofen, diazepam, griseofulvin, cyclosporin, cortisone, proleukin, etoposide and paclitaxel. Administration of chemotherapeutic or anti-cancer agents is particularly problematic. The majority of these agents are poorly soluble and thus are difficult to deliver in aqueous solvents and supply at therapeutically useful levels. On the other hand, water-soluble anti-cancer agents are generally taken up by both cancer and non-cancer cells, thereby exhibiting non-specificity. Oily drugs further include agents such as ubiquinone (CoQ-10), certain nutraceuticals, nutritional agents such betacarotene, various vitamins and vitamin derivatives such as vitamin A, vitamin $B_2$, vitamin D, vitamin E, vitamin K, prebiotics, probiotics, antiviral HIV protease inhibitors (e.g., Ritonavir, Saquinavir), therapeutic agents for hyperlipidemia (e.g., clofibrate), iodine compounds (e.g., sodium iopodate, sodium iodide), polyunsaturated fatty acid derivatives (e.g., ethyl eicosapentaenoic acid (EPA), docosahexaenoic acid (DHA)), carotenoids (e.g., lycopene, bixin, beta-carotene, xanthophyll, lutein), ubiquinones (coenzyme Q) (e.g., ubidecarenone used as a metabolizable cardiac stimulant), and the like. Prostaglandin and/or derivatives thereof, and the freebase form of pilocarpine also constitute oily drugs. Generally, drugs which are included in or which are candidates for inclusion in a soft gelatin capsule would be considered an oily active ingredient as defined herein. Other examples will be recognized by those skilled in the art.

Oily drugs present solubility problems in aqueous media, and they are not readily dispersed in such media. Historically, surfactants have been employed to form emulsions in which the oily drugs are dissolved or suspended. See U.S. Pat. No. 4,347,238. However, stability of the emulsion can then become a problem. Over time, oily particles forming the disperse phase of the emulsion can agglomerate or coalesce and separate from the aqueous continuous phase. The presence of salts and/or soluble polymers used to increase viscosity can exacerbate the problem by competing for water, thereby increasing the tendency of the oily disperse phase to separate from the aqueous continuous phase. Indeed, avoidance of large quantities (i.e., greater than 0.3%) of the salt of a lightly cross-linked polyacrylic acid has been recommended because of a tendency to gel the water phase, making the emulsion immobile. See U.S. Pat. No. 4,347,238 at col. 3, lines 7-10.

The oily drug(s) included in the compositions of the invention include compounds or compositions of matter which, when administered to an organism (human or animal) induce a desired pharmacological and/or physiologic elect by local and/or systemic action. In general, the terms include the therapeutic or prophylactic agents in all major therapeutic or prophylactic areas of medicine. A bioactive agent may be a phyto-chemical, drug, nutrition agent, Vitamin, peptide, oligonucleotide or liposaccharide or combinations thereof.

Classes of drugs which may be incorporated with the excipient of the present invention include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, antineoplastic agents, and cholesterol ester transfer protein inhibitors.

The present invention is useful with any drug capable of being formulated as an amorphous drug. The term "drug" is conventional, denoting a compound having beneficial prophylactic and/or therapeutic properties when administered to an animal, especially humans. The drug does not need to be a low-solubility drug in order to benefit from this invention, although low-solubility drugs represent a preferred class for use with the invention. Even a drug that nonetheless exhibits appreciable solubility in the desired environment of use can benefit from the increased solubility/bioavailability made possible by this invention if the formulation and administration in the presented carrier can reduce the size of the dose needed for therapeutic efficacy or increase the rate of drug absorption in cases where a rapid onset of the drug's effectiveness is desired.

The active ingredient(s) may further be any agent that is traditionally used as a medicament and lends itself to being administered through the oral cavity. Such active agents may be vitamins, chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, nutraceuticals and nutritional supplements.

Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K and Coenzyme Q10.

Example of botanical bioactive agents, are: polyphenols, isoflavones, resveratrol, soy isoflavones, grape seed extract polyphenols, curcumin, epigenin. Anti-inflammatory plant extracts such as aloe vera, echinacea and chamomile hammamelis extracts, anti-psoriatic such as chinese zizipus jujuba. Astringents such as hammamelis anti bacterial such as artemisia, chamomile, golden seal. Immune modulators such as echinacea, anti-aging or anti-cancer or anti-photo damage, anti-inflammatory such as feverfew parthenolides, rejuvenation agents, carotenoids, beta-carotene, lycopene, astaxanthons, lutein, tocopheryl and retinol.

Coronary drugs: including vasodilators such as nitroglycerin, isosorbide dinitrate, Calcium-antagonists such as verapamile, nifedipine and diltiazem, Cardiac-glycosides such as digoxine. Analgesics: eg. morphine, buprenorphine, etc; Local anaesthetics: eg. lidocaine, etc;

Example of cholesterol and triglycerides lowering drug: fenofibrate, lovastatin, simvastatin, pravastatin, fluvastatin, atorvastatin, or cerivastatin.

Anxiolytics, sedatives & hypnotics: diazepam, nitrazepam, flurazepam, estazolam, flunitrazepam, triazolam, alprazolarn, rnidazolarn, temazepam, lormetazeparn, brotizolam, clobazam, clonazepam, lorazepam, oxazepam, buspirone, etc; Migraine relieving agents: sumatriptan, ergotamines and derivatives etc; Drugs against motion sickness: eg. cinnarizine, anti-histamines, etc; Anti-emetics: eg. ondansetron, tropisetron, granisetrone, metoclopramide, etc. Others: such as disulfuram, vitamin K, etc.

Examples of chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin, daunorubicin, doxonibicin, bleomycin, plicornycin, mitomycin, etoposide (VP16), tamoxifen, taxol, transplatinum, 5-fluorouracil, vincristin, vinblastin and methotrexate or any analog or derivative variant thereof.

Example of antibiotics drugs: Tetracyclines such as tetracycline, doxycycline, oxytetracycline, chloramphenicol etc; Macrolides such as erythromycin and derivatives, etc; Antivirals: such as acyclovir, idoxuridine, tromantadine etc; Antimycotics: Miconazole, ketoconazole, fluconazole, itraconazole, econazole, terconazole, griseofulvin, and polyenes such as amphotericin B or nystatine etc; Anti-amoebics: Metronidazole, metronidazole benzoate and tinidazole etc; Anti-inflammatory drugs: steroids or NSAID's such as indomethacin, ibuprofen, piroxicam, diclofenac etc; Anti-allergies: Disodium cromoglycate etc; Immunosuppressive agents: cyclosporins etc;

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, .beta.-lactamase inhibitors; meziocillin, piperacillin, aztreonam, norfloxacin, trimethoprim, ceftazidime, ceftriaxone and dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscamet, ganciclovir, zidovudine, dideoxycytosine, dideoxyinosine, stavudine, famciclovir, didanosine, zalcitabine, rifimantadine, and cytokines.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prylamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan, levopropoxyphene napsylate, noscapine, carbetapentane, caramiphen, chlophedianol, pseudoephedrine hydrochloride, diphenhydramine, glaucine, pholcodine, and benzonatate.

Anesthetics include etomidate, ketamine, propofol, and benodiazapines (e.g., chlordiazepoxide, diazepam, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocaine, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloral hydrate, ethchlorvynol, clutethimide, methprylon, ethinamate, and meprobamate.

Analgesics, include opioids such as morphine, mepidine, dentanyl, sufentranil, alfentanil, aspirin, acetaminophen, ibuprofen, indomethacine, naproxen, atrin, isocome, midrin, axotal, firinal, phrenilin, ergot and ergot derivatives (wigraine, cafergot, ergostat, ergomar, dihydroergotamine), imitrex.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprionolactone, canrenone, and potassium canrenoate.

Anti-inflammatories include but are not limited to salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include thorazine, serentil, mellaril, millazine, tindal, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, eldepryl.

Cardiovascular agents include but are not limited to nitroglycerin, isosorbide dinitrate, sodium nitroprisside, captopril, enalapril, enalaprilat, quinapril, lisinopril, ramipril, losartan, aminone, liririone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, veraparnil, nifedipine, amlodipine and dobutamine.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

In embodiments in which the oily active ingredient is not a drug, the oil active ingredient may be disinfecting agents, chemical impregnants, cleansing agents, deodorants, fragrances, dyes, animal repellents, insect repellents, a fertilizing agents, pesticides, herbicides, fungicides, and plant growth stimulants, and the like.

The excipient of the present invention may be physically mixed with the oily active ingredient (e.g., oily drug) and other optional pharmaceutical excipients and thereafter either tableted or filled into a capsule in powder form. Alternatively, all or part of the excipient may be subjected to a wet granulation with the active ingredient. A representative wet granulation includes loading the novel excipient particles into a suitable granulator, such as those available from Baker-Perkins, and granulating the particles together with the active ingredient, preferably using an aqueous granulating Uquid. The granulating liquid is added to the mixture with stirring until the powdery mass has the consistency of damp snow and then wet screened through a desired mesh screen, for example, having a mesh from about 12 to about 16. The screened granulate is then dried, using standard drying apparatus such as a convection oven before undergoing a final screening. Additional dry screening of this material is possible, such as by using screens of from about 40 to about 200 mesh. Those materials flowing through 40 and 60 mesh screens may be further ground prior to ultimate tablet formulation. The thus obtained wet granulate containing novel excipient is now capable of undergoing tableting or otherwise placed into a unit dosage form.

In certain preferred embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with conventional microcrystalline cellulose, or other excipients commonly used by those skilled in the art, depending of course upon the requirements of the particular formulation.

In other embodiments of the invention, a further material is added to the slurry of microcrystalline cellulose in the form of a wet cake, silicate-based adsorbant, and optional compressibility enhancing agent, prior to drying (e.g., spray-drying). Such additional materials include non-silicon metal oxides, starches, starch derivatives, surfactants, polyalkylene oxides, cellulose ethers, celluloses esters and mixtures thereof. These additives may be included in desired amounts which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, in addition to the above ingredients, the solid formulations prepared using the novel excipient may also include suitable quantities of pharmaceutical adjuvants, e.g., diluents, plasticizers, lubricants, binders, granulating aids, disintegrants (e.g., sodium starch glycolate (commercially available from JRS Pharma under the tradename Explotab®), colorants, flavorants and glidants that are conventional in the pharmaceutical art. A non-limiting list of suitable adjuvants include spray dried lactose, polyvinylpyrrolidone (PVP), talc, magnesium stearate, and mixtures thereof. The quantities of these additional materials will be sufficient to provide the desired effect to the desired formulation. Other examples of pharmaceutically acceptable carriers and excipients that may be used to formulate oral dosage forms are described in the Handbook of Pharmaceutical Excipients, American Pharmaceutical Association (1986), incorporated by reference in its entirety.

A non-limiting list of plasticizers includes include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticizer.

For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like. An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5-3% by weight of the solid dosage form.

The complete mixture, in an amount sufficient to make a uniform batch of tablets, may then subjected to tabletting in a conventional production scale tabletting machine at normal compression pressures for that machine, e.g., about 1500-40,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

In certain embodiments, the tablets prepared using the novel excipient may comprise a homogeneous mixture of the novel excipient, oily active ingredient(s), and optional further active ingredient(s) and optional further excipients (e.g., pharmaceutically acceptable excipients where the oily active ingredient and/or optional further active ingredient(s) are a drug), or may comprise a compression coated tablet, in which the active substance is contained within a core which is contained within an outer coating (either hydrophobic coating or hydrophilic coating, e.g., as described below). In some embodiments, the coating may be complete, in other embodiments, the coating may be partial.

In certain embodiments of the present invention, the novel excipient and oily active ingredient are further prepared with one or more controlled or sustained release carriers to provide a delayed or sustained release of the active ingredient from the final product (e.g., oral tablet). This can be accomplished, e.g., by incorporating a sustained release carrier(s) together with the mixture of the novel excipient and oily drug(s) (with further optional active ingredients and or further optional pharmaceutically acceptable excipients) and then tableting the mixture, thereby obtained sustained release matrix tablets. On the other hand, the novel excipient and oily drug(s) (with further optional active ingredients and or further optional pharmaceutically acceptable excipients) may be tableted or filled into a capsule, which is then coated with one or more delayed (e.g., enteric) or sustained release carriers to thereby provide a delayed or sustained release final formulation.

In certain embodiments of the invention, the tablet is coated with a sufficient amount of a hydrophobic polymer to render the formulation capable of providing a release of the active ingredient(s) such that a 12 or 24 hour formulation is obtained. The hydrophobic polymer which included in the tablet coating may be the same or different material as compared to the hydrophobic polymeric material which is optionally granulated with the sustained release excipient.

In other embodiments of the present invention, the tablet coating may comprise an enteric coating material in addition to or instead or the hydrophobic polymer coating. Examples of suitable enteric polymers include cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. An example of a suitable commercially available enteric material is available under the trade name Eudragit®L 100-555.

In further embodiments, the dosage form may be coated with a hydrophilic coating in addition to or instead of the above-mentioned coatings. An example of a suitable material which may be used for such a hydrophilic coating is hydroxypropylmethylcellulose (e.g., Opadry®, commercially available from Colorcon, West Point, Pa.).

The coatings may be applied in any pharmaceutically acceptable manner known to those skilled in the art. For example, in one embodiment, the coating is applied via a fluidized bed or in a coating pan. For example, the coated tablets may be dried, e.g., at about 60-70° C. for about 3-4 hours in a coating pan. The solvent for the hydrophobic polymer or enteric coating may be organic, aqueous, or a mixture of an organic and an aqueous solvent. The organic solvents may be, e.g., isopropyl alcohol, ethanol, and the like, with or without water.

The coatings which may be optionally applied to the compressed solid dosage form of the invention may comprise from about 0.5% to about 30% by weight of the final solid dosage form.

In additional embodiments of the present invention, a support platform is applied to the tablets manufactured in accordance with the present invention. Suitable support platforms are well known to those skilled in the art. An example of suitable support platforms is set forth, e.g., in U.S. Pat. No. 4,839,177, hereby incorporated by reference. In that patent, the support platform partially coats the tablet, and consists of a polymeric material insoluble in aqueous liquids. The support platform may, for example, be designed to maintain its impermeability characteristics during the transfer of the therapeutically active medicament. The support platform may be applied to the tablets, e.g., via compression coating onto part of the tablet surface, by spray coating the polymeric materials comprising the support platform onto all or part of the tablet surface, or by immersing the tablets in a solution of the polymeric materials.

The support platform may have a thickness of, e.g., about 2 mm if applied by compression, and about 10 microns if applied via spray-coating or immersion-coating. Generally, in embodiments of the invention wherein a hydrophobic polymer or enteric coating is applied to the tablets, the tablets are coated to a weight gain from about 1% to about 20%, and in certain embodiments preferably from about 5% to about 10%.

Materials useful in the hydrophobic coatings and support platforms of the present invention include derivatives of acrylic acid (such as esters of acrylic acid, methacrylic acid, and copolymers thereof) celluloses and derivatives thereof (such as ethylcellulose), polyvinylalcohols, and the like.

In other embodiments of the invention which provide a sustained release product, the sustained-release carrier may be incorporated in a sustained-release matrix to impart sustained-release of the active agent from the final formulation. The sustained release carrier may be hydrophobic or hydrophilic. Suitable materials which may be included in the sustained release carrier of the present invention include alkylcelluloses such as natural or synthetic celluloses derivatives (e.g. ethylcellulose), acrylic and methacrylic acid polymers and copolymers, zein, and mixtures thereof. Suitable biocompatible, preferably biodegradable polymers can be utilized as the sustained release carrier. The biodegradable polymeric material may comprise a polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters, and polyorthoesters. The polysaccharides may be poly-1,4-glucans, e.g., starch glycogen, amylose, amylopectin, and mixtures thereof. The biodegradable hydrophilic or hydrophobic polymer may be a water-soluble derivative of a poly-1,4-glucan, including hydrolyzed amylopectin, hydroxyalkyl derivatives of hydrolyzed amylopectin such as hydroxyethyl starch (HES), hydroxyethyl amylose, dialdehyde starch, and the like.

In yet other preferred embodiments, sustained-release carrier comprises a synthetic or naturally occurring gum. Examples of naturally occurring gums include, e.g., the heteropolysaccharides and homopolysaccharides. An especially preferred heteropolysaccharide is xanthan gum, which is a high molecular weight (>10.sup.6) heteropolysaccharide. Other preferred heteropolysaccharides include derivatives of xanthan gum, such as deacylated xanthan gum, the carboxymethyl ether, and the propylene glycol ester. The homopolysaccharides useful in the present invention include galactomannan gums, which are polysaccharides composed solely of mannose and galactose. Preferred galactomannan gums are those which are capable of cross-linking with the heteropolysaccharide. In particular, galactomannans which have higher proportions of unsubstituted mannose regions have been found to achieve more interaction with the heteropolysaccharide when exposed to an environmental fluid. Locust bean gum, which has a higher ratio of mannose to galactose, is especially preferred as compared to other galactomannans such as guar and hydroxypropyl guar. Other natural or synthetic gums known to those skilled in the food and pharmaceutical arts are also useful as the controlled release carrier of the invention. Such gums include alginic acid derivatives, carageenan, tragacanth, acacia, karaya, guar gum, agar, acacia, galactans, mannans, and the like. Water swellable polymers may be used in addition to or instead of gums to promote sustained-release of the active agent from the final formulation. Such water swellable polymers include cellulose ethers, carboxyvinyl polymer and the like.

Optionally, the sustained-release carrier includes a release modifying agent. A release modifying agent according to the invention includes any pharmaceutically acceptable substance which my alter, e.g. prolong or increase, the release rate of the active agent form the formulation upon exposure to an aqueous environment, e.g. gastric fluid or dissolution medium. Suitable release modifying agents which may be incorporated into the matrix formulations of the present invention include, e.g., monovalent or multivalent metal cations. Preferably, the salts are inorganic salts, including e.g., alkali metal and/or alkaline earth metal sulfates, chlorides, borates, bromides, citrates, acetates, lactates, etc. In particular, these salts include, e.g., calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. In preferred embodiments, the release modifying agents are bivalent. Particularly preferred salts are calcium sulfate and sodium chloride. Other release modifying agents include sugars, e.g. sucrose, starches, water-soluble alkylcellulose derivatives such as hydroxypropylmethylcellulose, urea, and the like.

In those embodiments including a release modifying agent any effective amount may be employed (generally from about 0.1% to about 20%, by weight).

The final sustained-release oral dosage form may contain from about 1 to about 99% (by weight) of sustained release carrier. Preferably, the weight percent of the sustained release carrier ranges from about 1 to about 80%.

In certain preferred embodiments of the present invention, the sustained release carrier is a pharmaceutically acceptable acrylic polymer, including but not limited to acrylic acid and methacrylic acid copolymers, methyl methacrylate, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamine copolymer, poly(methyl methacrylate), poly (methacrylic acid)(anhydride), polymethacrylate, polyacrylamide, poly(methacrylic acid anhydride), and glycidyl methacrylate copolymers. In other embodiments, the sustained-release carrier may further include a relatively hydrophilic material, including but not limited to materials such as hydroxyalkylcelluloses such as hydroxypropylmethylcellulose and mixtures of the foregoing.

In yet another embodiment of the present invention, the sustained release carrier(s) (with or without optional release modifying agent(s)) is added into the aqueous slurry of the novel excipient, and the aqueous slurry is then dried in such a manner as to obtain agglomerated sustained release particles.

In certain embodiments of the present invention, the tablet core includes an additional dose of the same or different active ingredient in either the hydrophobic or enteric coating, or in an additional overcoating coated on the outer surface of the tablet core (without the hydrophobic or enteric coating) or as a second coating layer coated on the surface of the base coating comprising the hydrophobic or enteric coating material. This may be desired when, for example, a loading dose of a therapeutically active agent is needed to provide therapeutically effective blood levels of the active agent when the formulation is first exposed to gastric fluid. The loading dose of medicament included in the coating layer may be, e.g., from about 10% to about 40% of the total amount of medicament included in the formulation.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857-884, hereby incorporated by reference stabilizers, binders, odor controlling agents, and preservatives.

The excipient of the present invention provides significant advantages over the prior art with respect to oily active agents or drugs dissolved in an oil. For example, the excipient allows for a manufacturer to switch from expensive and slow soft-gel production to tableting. Also, physical stability issues often found with soft-gel capsules are avoided. Further, oily active agents can be administered in solution in a more dispersed fashion from a tablet than may be formulated to disintegrate faster than a bolus oil dose may disperse. The excipient of the present invention may also be used in allow for the use of SEDDS (self-emulsifying drug delivery system) and SMEDDS (self-microemulsifying drug delivery system) into tablets. This may provide the added benefit where the active agent is a drug of enhancing the bioavailability of the drug from the tableted formulation of the present invention over the comparable oil-dosed drug.

Alternatively, the novel excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

DETAILED DESCRIPTION OF THE PREFERRED EMBODIMENTS

The following examples illustrate various aspects of the present invention. They are not to be construed to limit the claims in any manner whatsoever.

EXAMPLE 1

Evaluation of a number of silicate-based adsorbents revealed compounds that had high oil-carrying capacity, and could retain a significant portion of this capacity when mechanical pressure was applied.

Physical blends of the components of microcrystalline cellulose (MCC), colloidal silicon dioxide (CSD), and one adsorbent added at various concentrations in the mixture, were prepared by simple blending to determine the level at which the adsorbent could be added to the proposed excipient without negatively impacting the compressibility of the resulting excipient. Neusilin® (magnesium alumino metasilicate, Fuji Chemical Co.) was chosen as the prototype adsorbent for the initial work, and olive oil was used as a surrogate for an oily drug. Initially, dry blends of JRS Prosolv® 50 (coprocessed MCC and CSD excipient blend) and various concentrations of Neusilin® were prepared with 0.5% Pruv® (sodium stearyl fumarate) as a lubricant. In later studies, the Prosolv® 50 and Neusilin® were co-processed. ProSolv SMCC 50 is a silicified microcrystalline cellulose composed of 98% microcrystalline cellulose and 2% colloidal silicon dioxide.

Although robust tablets could be produced with the level of Neusilin in the blend formulations reaching 50% of the level of Prosolv® 50, addition of olive oil (also by simple blending) to the blended excipient and subsequent compression into tablets, resulted in relatively soft, poor quality tablets. It was therefore considered desirable to conduct oil-loading studies starting with a higher level of Prosolv® 50 relative to the level of Neusilin® to improve the integrity of the tablets when loaded with oil, and titrate this level downward, while titrating oil content upward to evaluate maximum oil-carrying capacity. Tablets were prepared with the goal of maximizing oil content of a 500 mg tablet. Pruv® (sodium stearyl fumarate lubricant commercially available from JRS Pharma) was included for tableting. See Table 1, below.

TABLE 1

| Material | Mg/tablet | | | | |
|---|---|---|---|---|---|
| PROSOLV ® 50 | 354.4 | 341.9 | 329.4 | 316.9 | 304.4 |
| Neusilin ® US2 | 80.6 | 80.6 | 80.6 | 80.6 | 80.6 |
| PRUV ® | 2.5 | 2.5 | 2.5 | 2.5 | 2.5 |
| Olive oil | 62.5 | 75 | 87.5 | 100 | 112.5 |
| Tablet weight | 500 | 500 | 500 | 500 | 500 |
| Tablet Oil Content (mg oil/mg tablet) | 100/800 | 100/667 | 100/571 | 100/500 | 100/444 |

As can be seen from Table 1, the amount of silicate-based adsorbent carrier (e.g., magnesium alumino metasilicate (e.g., Neusilin®)) relative to the amount of MCC and CSD (combined) was from about 26.5% to about 22.7%. Another way of expressing the ingredients included in the excipient of Example 1 is that the excipient included from about 18.5% to about 20.9% silicate-based adsorbent carrier (e.g., magnesium aluminometasilicate (e.g., Neusilin®), and from about 1.58% to about 1.63% compressibility augmenting agent (e.g., CSD).

Compression profiles were generated for the above blend formulations. See FIG. 1.

EXAMPLE 2

Next, two of the three blend formulations of Example 1 having the highest oil content were duplicated, this time using co-processing. See Table 2 below.

TABLE 2

| Co-Processed Prosolv Oil Excipient Formulations | | |
|---|---|---|
| Material | Mg/tablet | |
| Formulation | 1 | 2 |
| PROSOLV 50 | 329.4 | 316.9 |
| Neusilin US2 | 80.6 | 80.6 |
| Tablet Oil Content (mg oil/mg tablet) | 100/571 | 100/500 |

Formulations 1 and 2 were co-processed by combining the ingredients in a slurry with water at a solids content of 15-20%. Thereafter, additional water is added to bring the slurry to around 15% solids content. Thereafter, the slurry is spray-dried at 200° C. inlet and 105° C. outlet at 31.2 Hz.

Figure 2:
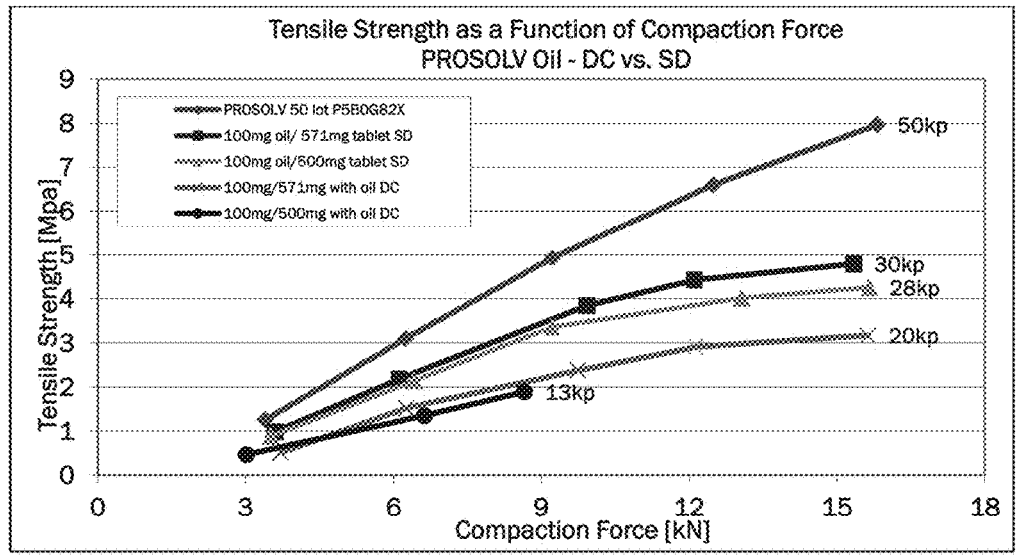
FIG. 2 graphically shows comparative compression profiles of the Prosolv Oil Excipient—Co-Processed (SD) versus Simple Blends (DC) of Example 2.

The resulting compression profiles of the co-processed materials were compared with those of the same formulations produced by simple blending, and are shown in FIG. 2. It is clear from FIG. 2 that when co-processed, the resulting Prosolv Oil formulations exhibit improved compression profiles over those produced by simple blending.

The amount of Neusilin included in the excipient was about 25% of the MCC for formulation 1 and about 26% of the MCC for formulation 2. The amount of Neusilin included in the excipient was about 19.66% in formulation 1 and about 20.28% in formulation 2. The amount of MCC in the excipient of formulation 1 was about 78.73% and about 78.14% in formulation 2. The amount of CSD in the excipient of formulation 1 was about 1.61% in formulation 1 and 1.59% in formulation 2.

With respect to the tableted formulations of Example 2, the amount of MCC in the tablets was about 56.53% in formulation 1 and about 62.16% in formulation 2. The amount of CSD in the tableted formulations of Example 2 was about 1.15% in formulation 1 and about 1.28% in formulation 2. The amount of Neusilin in the tableted formulations was about 14.12% in formulation 1 and about 16.12% in formulation 2. The amount of oily active agent (based on the olive oil surrogate) included in the tableted formulations was about 17.5% in formulation 1 and about 20% in formulation 2.

EXAMPLE 3

Using MCC, CSD, and a metal alumino metasilicate (Neusilin®), physical mixtures of an excipient in accordance with the present invention was made by (i) physically mixing these ingredients, and (ii) preparing co-processed blends of these ingredients. The ingredients of the excipient are set forth in Table 3.

TABLE 3

| Ingredient | % included | Batch Size (kg) | Solid slurry contribution (%) | lbs |
|---|---|---|---|---|
| MCC | 78.10 | 1.562 | 11.32 | 3.4364 |
| Cab-o-Sil M5P | 1.60 | 0.032 | 0.23 | 0.0704 |
| Neusilin US2 | 20.3 | 0.406 | 2.94 | 0.8932 |
| Slurry total | 0 | 0 | 14.5 | 4.4 |
| Dry addition total | 0 | 0 | | 0 |
| Powder total | 100 | 2.0 | | 4.4 |

In order to manufacture the slurry, the microcrystalline cellulose (MCC) slurry was prepared. The colloidal silicon dioxide (CSD) was added to the MCC slurry. Next, the Neusilin US2 was added to the slurry containing the MCC and CSD. Next, the required water was added to achieve the following: The solids content of the MCC slurry was 18.60%. The required weight of the MCC slurry in kg was 8.40%. The MCC solids content was 11.32%. The required water added (kg) was 5.4. The total water weight (kg) was 12.23. The total slurry weight (kg) was 13.79. The overall slurry solids target was 14.50%. Thereafter, the slurry was spray-dried at 200° C. inlet and 105° C. outlet at 31.2 Hz.

The excipient will carry as much as 100 mg of oil or more (olive oil used as a surrogate for an oily active ingredient) in a 500 mg tablet. Tablets can be compressed with high application of force without fouling the punches and result in trouble free compression. The presence of oil in the mix does reduce the hardness somewhat (as compared to a mixture not containing oil), but not to the extent that tablet quality is compromised. The co-processed (slurry) blends showed a slightly higher oil carrying capacity that the physical mixtures, and produced very satisfactory tablets.

EXAMPLE 4

An excipient in accordance with the present invention included the following ingredients set forth in Table 4.

TABLE 4

| Component | % w/w |
|---|---|
| Prosolv 50 | 79.72 |
| Neusilin US2 | 20.28 |
| Total | 100.00 |

The excipient is prepared by preparing an aqueous slurry of the Prosolv 50 (containing MCC and 2% CSD). Thereafter, the magnesium alumino metasilicate (Neusilin US2) is added to the slurry. Then, the slurry containing all three ingredients (MCC, CSD and magnesium alumino metasilicate) is spray-dried to produce the ready-to-use excipient.

The amount of Neusilin included in the excipient was about 26% of the MCC for Example 4. The amount of Neusilin included in the excipient was about 20.28%, the amount of CSD was about 1.59% and the amount of MCC was about 78.13% of the excipient.

EXAMPLE 5

An excipient in accordance with the present invention included the following ingredients set forth in Table 5.

TABLE 5

| Component | % w/w |
|---|---|
| Microcrystalline cellulose | 77.72 |
| Colloidal silicon dioxide | 2.00 |
| Neusilin US2 | 20.28 |
| Total | 100.00 |

The excipient is prepared by combining the ingredients in an aqueous slurry. Then, the slurry containing all three ingredients (MCC, CSD and magnesium alumino metasilicate) is spray-dried to produce the ready-to-use excipient.

EXAMPLE 6

In Example 6, the excipient prepared in either of Examples 4 or 5 is added to a suitable high-shear mixer. The ingredients are combined in the proportions set forth in Table 6.

TABLE 6

| Component | mg/tablet |
|---|---|
| Olive oil | 100 |
| Oil Excipient (of Example 4 or 5) | 397.5 |
| Pruv ® | 2.5 |
| Tablet weight | 500.00 mg |

While mixing, an oily active ingredient (olive oil can is used as a surrogate for an oily active ingredient) is added to the excipient and the ingredients are mixed until all of the oil is adsorbed and a free-flowing powder results, e.g., about 5 minutes. The free-flowing powder is then compressed into a tablet or filled into capsules as desired. When compressed into a tablet, this can be accomplished, e.g., on a Piccola 284 automated press at 5 different forces: approximately 3, 6, 9, 12 and 15 KN. For example, the tablet punch size is 0.5 inches and the targeted tablet weight is 500 mg using a gravity feeder and feed rate of 25 rpm. The tablet hardness at each compression force is measured, e.g., on a Sotax HT10 hardness tester.

The amount of Neusilin included in the tablet was about 16% w/w.

EXAMPLE 7

In Example 7, an excipient for an oily active ingredient is prepared in accordance with the above examples, except that Aeroperl® is included in place of Neusilin®. In Example 7, four formulations differing in ratios of Prosolv® 50 to Aeroperl were physically blended and evaluated for compaction. The formulations are set forth in Table 7 below.

TABLE 7

| Material | % of Formulation | weight (g) |
|---|---|---|
| 80/20 (Prosolv50:Aeroperl 300) - Original Formula as developed with Neusilin | | |
| Prosolv | 80.0 | 400.0 |
| Aeroperl 300 Pharma | 20.0 | 80.0 |
| Total | 100.0 | 500.0 |
| 75/25 (Prosolv50:Aeroperl 300) | | |
| Prosolv | 75.0 | 375.0 |
| Aeroperl 300 Pharma | 25.0 | 125.0 |
| Total | 100.0 | 500.0 |
| 70/30 (Prosolv50:Aeroperl 300) | | |
| Prosolv | 70.0 | 350.0 |
| Aeroperl 300 Pharma | 30.0 | 150.0 |
| Total | 100.0 | 500.0 |
| 65/35 (Prosolv50:Aeroperl 300) | | |
| Prosolv | 65.0 | 325.0 |
| Aeroperl 300 Pharma | 35.0 | 175.0 |
| Total | 100.0 | 500.0 |

Figure 3:
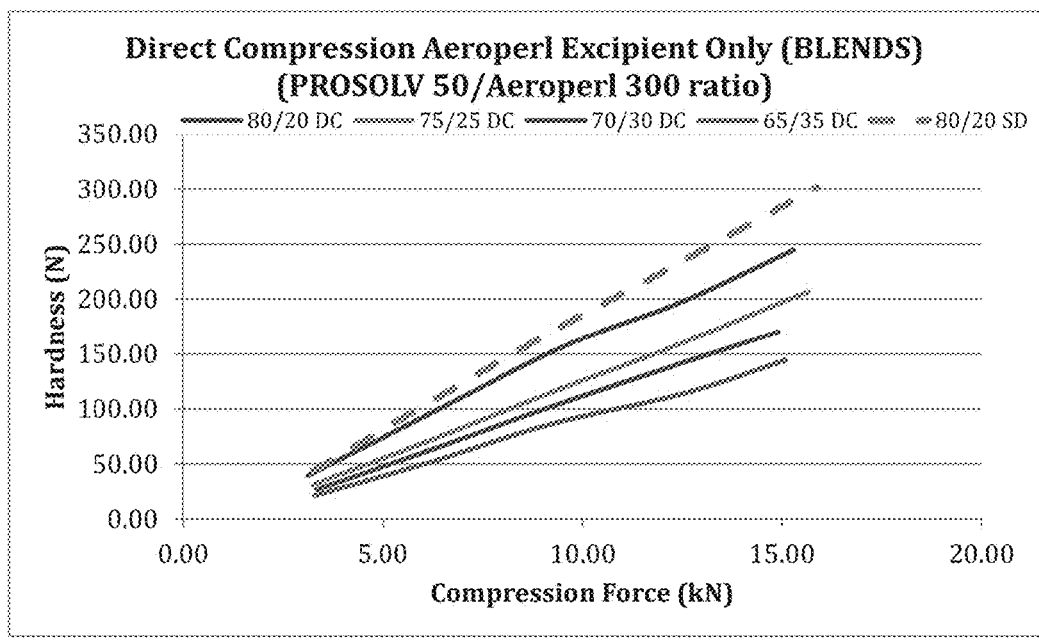
FIG. 3 graphically shows comparative direct compression profiles of the Prosolv Oil Excipient in different ratios of ProSolv 50 to Aeroperl 300 of Example 7 (physical blends)

The compaction of the physical blends were tested as compared to one spray-dried lot (80:20 Prosolv50:Aeroperl 300). The results are depicted in FIG. 3. As can be seen from the results depicted therein, the compaction decreased as Aeroperl content increased. Also, the co-processed (spray-dried) material (80:20 ratio) had higher compaction than the blended (physical mix) material (80:20 ratio). The data suggests that higher compression forces will yield higher hardnesses (a plateau level was not reached).

EXAMPLE 8

In Example 8, the oil loading capacity of an excipient including Aeroperl was tested. Therein, physical blends of Prosolv:Aeroperl were prepared at 80:20, 73:25, 70:30, and 65:35 as physical blends, and then the oil loading capacity of these excipients were tested using an oily active ingredient (olive oil can) as a surrogate for an oily active ingredient. The olive oil is added to the excipient and the ingredients are mixed until all of the oil is adsorbed and a free-flowing powder results, e.g., about 5 minutes. The free-flowing powder is then compressed into a tablet or filled into capsules as desired. Pruv® (sodium stearyl fumarate lubricant commercially available from JRS Pharma) was included for tableting. When compressed into a tablet, this can be accomplished, e.g., on a Piccola 284 automated press at 5 different forces: approximately 3, 6, 9, 12 and 15 KN. For example, the tablet punch size is 0.5 inches and the targeted tablet weight is 500 mg using a gravity feeder and feed rate of 25 rpm. The tablet hardness at each compression throe is measured, e.g., on a Sotax HT10 hardness tester. The formulations are provided in Table 8.

TABLE 8

Oil Loading of Blend Formulations

| Material (Prosolv:Aeroperl) | 80:20 (mg) | 75:25 (mg) | 70:30 (mg) | 65:35 (mg) |
|---|---|---|---|---|
| Olive Oil | 100 | 100 | 100 | 100 |
| Prosolv Oil Blend | 397.5 | 397.5 | 397.5 | 397.5 |
| PRUV (SSF) | 2.5 | 2.5 | 2.5 | 2.5 |
| Tablet wt (mg) | 500 | 500 | 500 | 500 |

Figure 4:
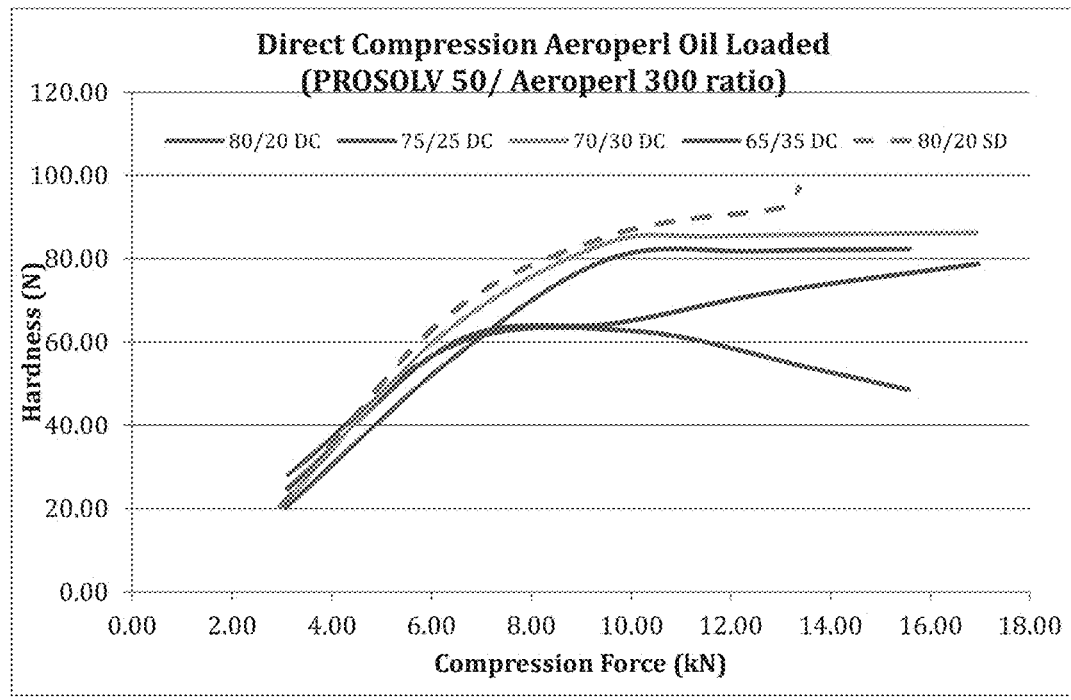
FIG. 4 graphically shows comparative compression profiles of the Prosolv Oil Excipient with oil loading of Example 8.

Next, the compaction of oil-loaded physical blends was tested. The results are provided in FIG. 4. The results show that when oil loaded, blended materials still do not achieve the same compaction as co-processed materials do. Unlike the examples which utilized Neusilin, as the silicate-based adsorbant carrier, as the Aeroperl content increased compaction increased to a point (65:35 and 70:30 ratios nearly equivalent). These were the best ratios tested. For these ratios (70:30 & 65:35) tablet hardness plateau was reached at about 80 newtons of hardness.

EXAMPLE 9

In Example 9, the formulation blends of Example 8 were prepared again, this time as co-processed materials. The spray drying process begins with an MCC slurry of a determined percent of solids about 19% in Example 9). Both CSD and adsorbent (Aeroperl 300 Pharma) were added to this slurry, along with additional water to yield a slurry with a final level of solids between about 14-15%. The solids level may vary depending upon the capability of the spray dryer or the contribution of an adsorbent to the viscosity of the slurry to be sprayed. Three separate spray drying experiments were performed, altering the level of Prosolv50/Aeroperl 300: 75/25, 70/30, and 65/35, along with the standard 80/20. All weights are based on 2.5 kg batches, on a dried basis, and a final solids level of the slurry, of 14%. The formulations are further described in Table 9.

TABLE 9

| Material | % of Formulation | Dried weight (kg) | Water contribution (kg) |
|---|---|---|---|
| 75/25 (Prosolv50:Aeroperl 300) | | | |
| MCC slurry, 19% solids | 73.5 | 1.838 | 7.834 |
| CSD | 1.5 | 0.038 | N/A |
| Aeroperl 300 Pharma | 25.0 | 0.625 | N/A |
| Additional Water add | N/A | N/A | 7.52 |
| 70/30 (Prosolv50:Aeroperl 300) | | | |
| MCC slurry, 19% solids | 68.6 | 1.715 | 7.311 |
| CSD | 1.4 | 0.035 | N/A |
| Aeroperl 300 Pharma | 30.0 | 0.750 | N/A |
| Additional Water add | N/A | N/A | 8.05 |
| 65/35 (Prosolv50:Aeroperl 300) | | | |
| MCC slurry, 19% solids | 63.7 | 1.593 | 6.789 |
| CSD | 1.3 | .033 | N/A |
| Aeroperl 300 Pharma | 35.0 | 0.875 | N/A |
| Additional Water add | N/A | N/A | 8.57 |
| 80/20 (Prosolv50:Aeroperl 300) | | | |
| MCC slurry, 19% solids | 78.1 | 1.953 | 8.324 |
| CSD | 1.6 | 0.04 | N/A |
| Aeroperl 300 Pharma | 20.3 | 0.508 | N/A |
| Additional Water add | N/A | N/A | 7.03 |

Figure 5:
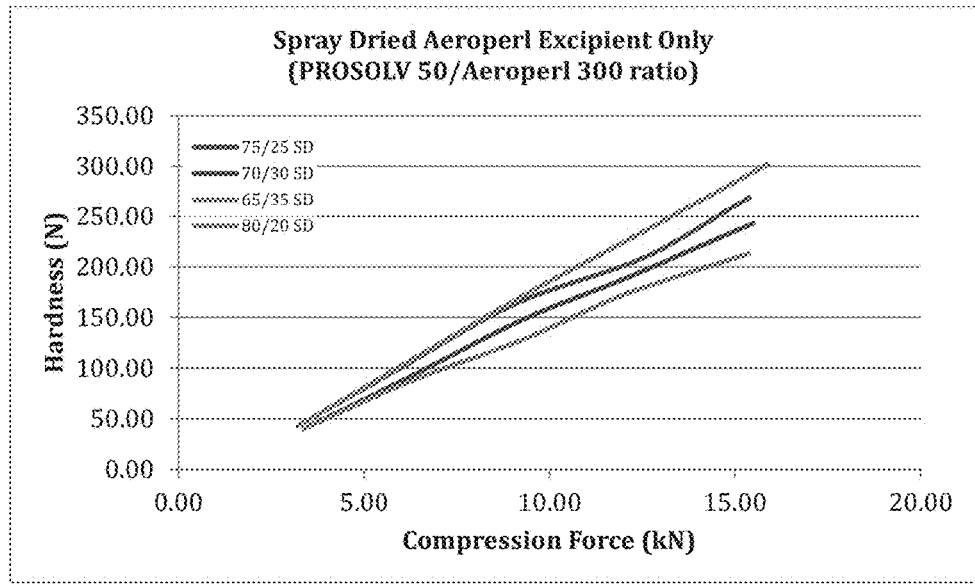
FIG. 5 graphically shows comparative compression profiles of the Prosolv Oil Excipient—co-processed of Example 9.

Tablets of the formulations of Example 9 were then compressed and evaluated for compaction. The results are provided in FIG. 5. As was true with blends, the compaction decreased as Aeroperl content increased. Also as observed with blends, the data suggests that higher compression forces will yield higher hardnesses (plateau not reached).

EXAMPLE 10

In Example 10, the co-processed materials of Example 9 were loaded to a 20% level with olive oil. The formulations of Example 10 are set forth in Table 10.

TABLE 10

Oil Loading of CO-Processed Materials

| Material (Prosolv:Aeroperl) | 80:20 (mg) | 75:25 (mg) | 70:30 (mg) | 65:35 (mg) |
|---|---|---|---|---|
| Olive Oil | 100 | 100 | 100 | 100 |
| Prosolv Oil Co-Processed excipient | 397.5 | 397.5 | 397.5 | 397.5 |
| PRUV (SSF) | 2.5 | 2.5 | 2.5 | 2.5 |
| Tablet wt (mg) | 500 | 500 | 500 | 500 |

Figure 6:
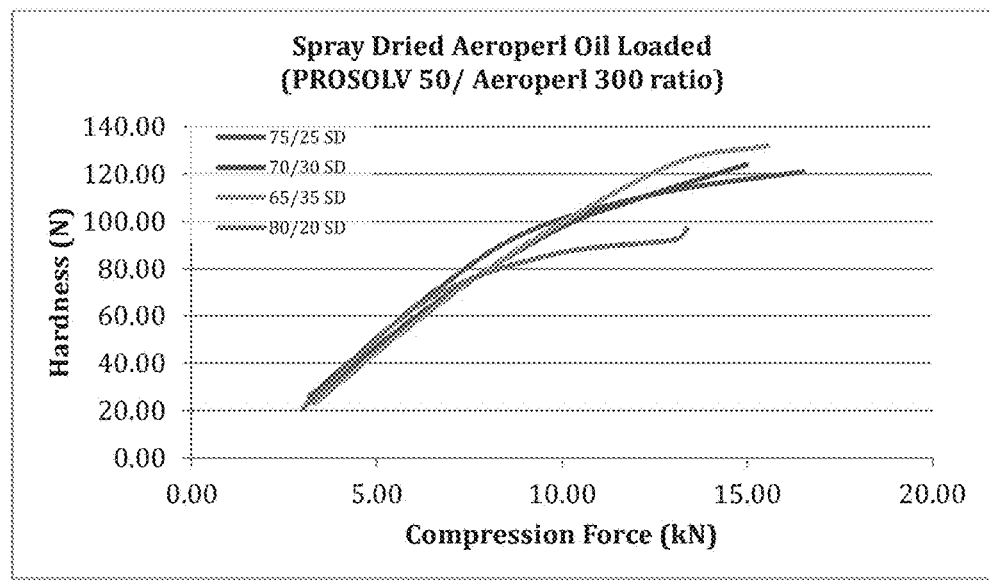
FIG. 6 graphically shows comparative compression profiles of the Prosolv Oil Excipient—co-processed with oil loading of Example 10.

Tablets were compressed and evaluated for compaction. The results are presented in FIG. 6. As can be seen from FIG. 6, the co-processed materials yield higher tablet hardnesses than was observed with physical blends. Similar to the physical blends, higher Aeroperl content yielded higher hardnesses in the co-processed materials. The data suggests that higher compression forces will yield higher hardnesses (@120 newtons (plateau not reached).

EXAMPLE 11

In Example 11, having established that co-processed material prepared at the various ratios studied could produce satisfactory tablets at a 20% oil load, formulations having an oil loading that exceeded the 20% limit of Example 9 were prepared and tested. For this, the co-processed material having the 65:35 ratio of MCC:Aeroperl was selected to give the highest chances for success. The formulations are set forth in Table 11.

TABLE 11

65/35 (Prosolv50:Aeroperl 300) at Various Oil Levels Tablet Formulations

|  | 65/35 (Prosolv 50:Aeroperl 300) | | | 80/20 (Prosolv50:Aeroperl 300) For comparison |
| --- | --- | --- | --- | --- |
| Material | 25% Oil Load (mg) | 30% Oil Load (mg) | 35% Oil Load (mg) | 20% Oil Load (mg) |
| Olive Oil | 125 | 150 | 175 | 100 |
| Prosolv Oil Excipient | 372.5 | 347.5 | 322.5 | 397.5 |
| PRUV (SSF) | 2.5 | 2.5 | 2.5 | 2.5 |
| Tablet wt (mg) | 500 | 500 | 500 | 500 |

Note:
% of oil load refers to % of oil in the overall tablet

The formulations of Example 11 are described in further detail in Table 12:

TABLE 12

|  | 65/35 (Prosolv50:Aeroperl 300) | | | 80/20 (Prosolv50:Aeroperl 300) For comparison |
| --- | --- | --- | --- | --- |
| Material | 25% Oil Load (mg) | 30% Oil Load (mg) | 35% Oil Load (mg) | 20% Oil Load (mg) |
| Olive Oil | 125 | 150 | 175 | 100 |
| MCC | 237.3 | 221.4 | 205.4 | 310.5 |
| CSD | 4.8 | 4.5 | 4.2 | 6.3 |
| Aeroperl 300 | 130.4 | 121.6 | 112.9 | 80.7 |
| PRUV (SSF) | 2.5 | 2.5 | 2.5 | 2.5 |
| Tablet wt (mg) | 500 | 500 | 500 | 500 |

Figure 7:
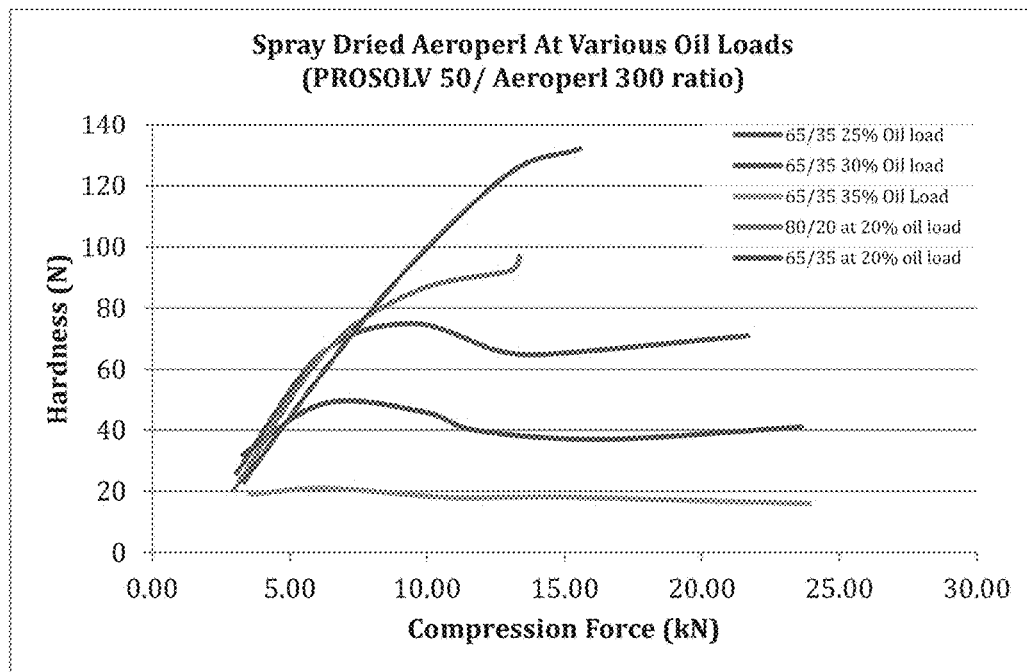
FIG. 7 graphically shows comparative compression profiles of the Prosolv Oil Excipient—co-processed with higher oil loadings of Example 11.

Tablets were compressed and evaluated for compaction. The results are presented in FIG. 7. As can be seen from FIG. 7, despite the high (35%) Aeroperl content, oil-loading of 25% or more yields tablets of reduced hardness which decreases further with increased oil loading and reflect the reduced oil carrying capacity of the Aeroperl versus Neusilin (1.9 g/g vs 3.2 g/g respectively). It can also be seen that the 65:35 ratio clearly out-performs the 80:20 ratio in oil-loading vs. hardness. This produces a very satisfactory scenario where oil-loading can be balanced against tablet hardness.

EXAMPLE 12

In Example 12, an excipient product consisting of cellulose and granulated hydrophilic fumed silicate (Aeroperl 300 Pharma) (as compared to an excipient product consisting of cellulose, granulated hydrophilic fumed silicate and colloidal silicon dioxide in previous examples). Accordingly, a slurry was prepared as per the previous examples using only Cosmo 92-40 pulp and Aeroperol 300 Pharma in a ratio of 65:35 as shown in Tables 13 and 14 below. The desired solids content of the slurry was 14.00%.

TABLE 13

Slurry Formulation

| Description | Solids Content | % Formulation | Dried Weight | Water Contribution | Required Wt (kg) |
| --- | --- | --- | --- | --- | --- |
| Cosmo 92-40 | 19.00% | 65.00% | 1.950 | 8.313 | 10.263 |
| TOTAL: | 9.10% | 65.00% | 1.950 | 8.313 | 10.263 |

TABLE 14

Ingredients added to the Slurry

| Description | % Formulation | Solids Contribution | Required Wt (kg) |
| --- | --- | --- | --- |
| Aeroperl 300 Pharma | 35.00% | 4.90% | 1.050 |
| TOTAL: | 35.00% | 4.90% | 1.050 |
| GRAND TOTAL: | 100.00% |  | 11.313 |

Additional water was required when the Aeroperl 300 was added (10.12), bringing the total water weight to 18.4 kg and the total slurry weight to 21.4 kg. The mixture was then spray dried as in the other co-processed examples. Thereafter, the resultant excipient was loaded with olive oil, and the mixture was tableted as per the above examples. The olive oil was added at an amount such that the olive oil comprised 20% of the tablet weight.

Figure 8:
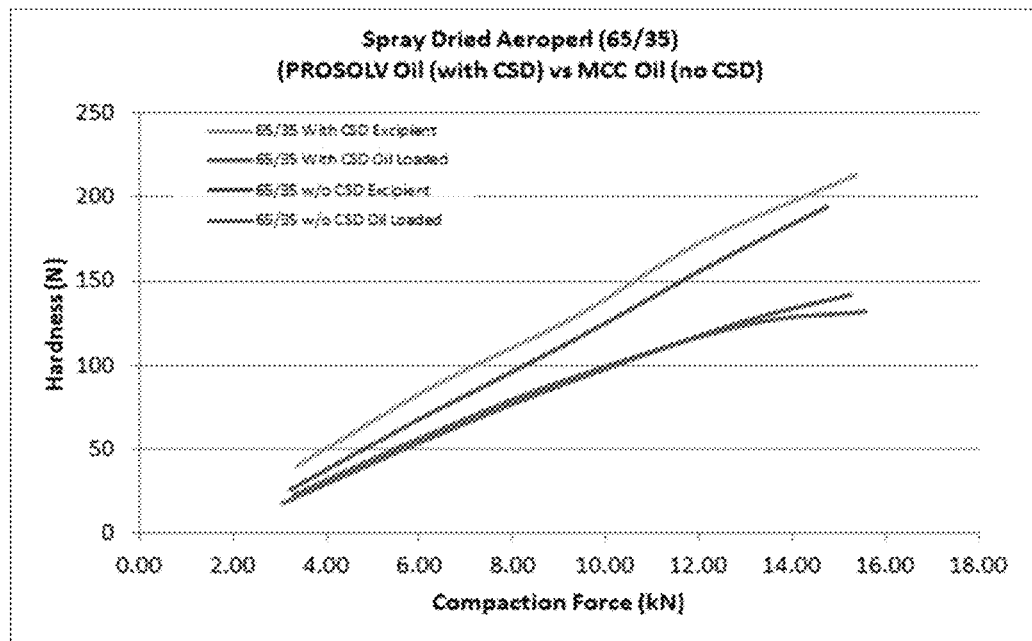
FIG. 8 graphically shows comparative compression profiles of the Prosolv Oil Excipient of Example 12—coprocessed with and without the presence of colloidal silicon dioxide, and with and without oil loading.

As a comparison, an additional product was made with 2% colloidal silicon dioxide incorporated therein. Both products contained nominally 35% Aeroperl 300 Pharma. Thereafter, a compaction study was run on the resulting blend (tablet). The results are depicted in FIG. 8. The plot below shows that compaction of the excipients alone (no oil load) resulted in higher hardness than oil-loaded excipients, with the excipient containing the colloidal silicon dioxide giving harder tablets across the range studied. Compaction of the oil-loaded excipients resulted in the same hardness values across the range studied, regardless of the presence of colloidal silicon dioxide. It is hypothesized that the effect of having the colloidal silicon dioxide in the excipient, is evident only when there is no oil load, that is, oil-loading evidently loads the colloidal silicon dioxide (Cab-O-Sil) as well, and therefore cancels its bonding effect (presumed to be hydrogen bonding) which would otherwise increase tablet hardness. Cab-O-Sil is also a mesoporous silica and shares the affinity for oily compounds.

EXAMPLE 13

In Example 13, an excipient product consisting of cellulose and magnesium alumino metasilicate (Neusilin US2) (as compared to an excipient product consisting of cellulose, granulated hydrophilic fumed silicate and colloidal silicon dioxide in previous examples). Accordingly, a slurry was prepared as per the previous examples using only Cosmo 92-40 pulp (microcrystalline cellulose) and Neusilin US2 in a ratio of 80:20 microcrystalline cellulose to magnesium alumino metasilicate. As a comparison, an additional product was made with 2% colloidal silicon dioxide incorporated therein. Both products contained nominally 20% magnesium alumino metasilicate. The mixture was spray-dried and tableted.

Figure 9:
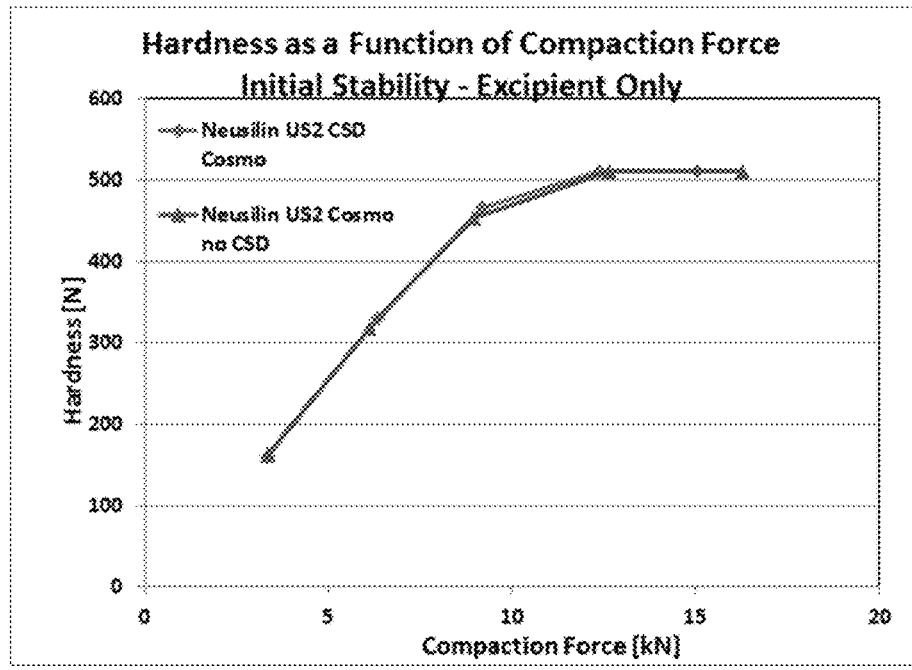
FIG. 9 graphically shows comparative compression profiles of the Prosolv Oil Excipient of Example 13 co-processed with and without the presence of colloidal silicon dioxide.

Thereafter, a compaction study was nm on the resulting blend (tablet). The results are depicted in FIG. 9. As can be seen from the plot, the two products had hardness curves that were substantially superimposable.

CONCLUSION

All of the percentages in the specification and specifically in the Examples provided above are expressed as w/w unless otherwise indicated. All of the patents mentioned herein are hereby incorporated by reference in their entireties.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. An excipient composition, consisting of microcrystalline cellulose and silicate-based adsorbent carrier selected from the group consisting of a magnesium aluminometasilicate, a granular hydrophilic fumed silica, and a mixture thereof, and optionally a colloidal silicon dioxide, wherein the amount of silicate-based adsorbant carrier is from about 10% to about 35% by weight of the excipient composition.

2. The excipient composition of claim 1, wherein the silicate-based adsorbent carrier is a magnesium aluminometasilicate.

3. The excipient composition of claim 1, wherein the silicate-based adsorbent carrier is a granular hydrophilic fumed silica.

4. The excipient composition of claim 1, which comprises from about 15% to about 35% silicate-based adsorbent carrier.

5. The excipient composition of claim 2, which comprises from about 12% to about 23% silicate-based adsorbent carrier.

6. The excipient composition of claim 3, wherein the amount of silicate-based adsorbent carrier is from about 20% to about 35% silicate-based adsorbant carrier.

7. The excipient composition of claim 1, which has an average particle size from about 10 nm to about 150 microns.

8. The excipient composition of claim 6, wherein the microcrystalline cellulose and the silicate-based adsorbent carrier are in the form of agglomerated particles comprising the same.

9. The excipient composition of claim 8, which is prepared by preparing an aqueous slurry of microcrystalline cellulose and silicate-based adsorbent carrier in the form of a wet cake, and spray-drying the ingredients to form agglomerated particles comprising the same.

10. The excipient composition of claim 1, wherein said colloidal silicon dioxide is included in an amount of from greater than 1% to about 5%, by weight.

11. An excipient composition, consisting of particles of microcrystalline cellulose, from about 15% to about 35% of a silicate-based adsorbent carrier selected from the group consisting of a magnesium aluminometasilicate, a granular hydrophilic fumed silica, and a mixture thereof, and from greater than 1% to about 20% colloidal silicon dioxide, by weight.

12. The excipient composition of claim 11, wherein the silicate-based adsorbent carrier is a magnesium aluminometasilicate.

13. The excipient composition of claim 11, wherein the silicate-based adsorbent carrier is a granular hydrophilic fumed silica.

14. The excipient composition of claim 11, wherein the particles of microcrystalline cellulose, silicate-based adsorbent carrier and colloidal silicon dioxide are agglomerated such that the ingredients are in intimate association with each other.

15. The excipient composition of claim 14, wherein the silicate-based adsorbent carrier is a magnesium aluminometasilicate.

16. The excipient composition of claim 14, wherein the silicate-based adsorbent carrier is a granular hydrophilic fumed silica.

* * * * *